United States Patent
Pedersen et al.

(10) Patent No.: US 10,590,468 B2
(45) Date of Patent: Mar. 17, 2020

(54) METHOD FOR METHYLATION ANALYSIS

(71) Applicant: CLINICAL GENOMICS PTY LTD, New South Wales (AU)

(72) Inventors: Susanne Pedersen, New South Wales (AU); Rohan Baker, New South Wales (AU)

(73) Assignee: CLINICAL GENOMICS PTY LTD, Elsternwick (AU)

( * ) Notice: Subject to any disclaimer, the term of this patent is extended or adjusted under 35 U.S.C. 154(b) by 80 days.

(21) Appl. No.: 15/315,931

(22) PCT Filed: Jun. 1, 2015

(86) PCT No.: PCT/AU2015/050297
§ 371 (c)(1),
(2) Date: Dec. 2, 2016

(87) PCT Pub. No.: WO2015/184498
PCT Pub. Date: Dec. 10, 2015

(65) Prior Publication Data
US 2017/0145485 A1    May 25, 2017

(30) Foreign Application Priority Data
Jun. 5, 2014 (AU) .............................. 2014902155

(51) Int. Cl.
C12Q 1/68       (2018.01)
C12Q 1/6827     (2018.01)
C12Q 1/6886     (2018.01)

(52) U.S. Cl.
CPC ......... *C12Q 1/6827* (2013.01); *C12Q 1/6886* (2013.01); *C12Q 2600/154* (2013.01)

(58) Field of Classification Search
None
See application file for complete search history.

(56) References Cited

FOREIGN PATENT DOCUMENTS

WO      00/70090 A1    11/2000
WO      2013/166558 A1  11/2013
WO      2015/014759 A1  2/2015

OTHER PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Baker R.T. et al., "Detection of Variable Methylation Patterns Improves Sensitivity of a Colorectal Cancer Blood Test", Gastroenterology 148(4, supp 1):S-747, AGA Abstracts (2015).
Beaucage S.L. et al., "Deoxynucleoside Phosphoramidites—A New Class of Key Intermediates for Deoxypolynucleotide Synthesis", Tetrahedron Letters 22(20)1859-1862 (1987).
Breslauer K.J. et al., "Predicting DNA Duplex Stability from the Base Sequence", Proc. Natl. Acad. Sci. USA 33:3746-3750 (Jun. 1986).
Caruthers M.H. et al., "Chemical Synthesis of Deoxyoligonucleotides by the Phosphoramidite Method", Methods in Enzymology 154:287-313 (1987).
Cottrell S.E et al., "A Real-Time PCR Assay for DNA-Methylation Using Methylation-Specific Blockers", Nucleic Acids Research 32(1):e10 (2004).
Eads C.A. et al., "MethyLight: A High-Throughput Assay to Measure DNA Methylation", Nucleic Acids Research 28 (8):e32 (2000).
Egholm M. et al., "PNA Hybridizes to Complementary Oligonucleotides Obeying the Watson-Crick Hydrogen-Bonding Rules", Nature 365:566-568 (Oct. 7, 1993).
Egholm M. et al., "Peptide Nucleic Acids (PNA). Oligonucleotide Analogues With an Achiral Peptide Backbone", J. Am. Chem. Soc. 114:1895-1897 (1992).
Gibson U E.M. et al., "A Novel Method for Real Time Quantitative RT-PCR", Genome Research 6:995-1001 (1996).
Heid C.A. et al., "Real Time Quantitative PCR", Genome Research 6:986-994 (1996).
Hill F. et al., "Polymerase Recognition of Synthetic Oligodeoxyribonucleotides Incorporating Degenerate Pyrimidine and Purine Bases", Proc. Natl. Acad. Sci. USA 95:4258-4263 (Apr. 1998).
Holland P.M. et al., "Detection of Specific Polymerase Chain Reaction Product by Utilizing the 5'-3' Exonuclease Activity of Thermus Aquaticus DNA Polymerase", Proc. Natl. Acad. Sci. USA 88:7276-7280 (Aug. 1991).
Lee L.G. et al., "Allelic Discrimination by Nick-Translation PCR With Fluorogenic Probes", Nucleic Acids Research 21 (16):761-3766 (1993).
Liu J. et al., "Methylation Modifications in Eukaryotic Messenger RNA", Journal of Genetics and Genomics 41:21-33 (2014).
Livak K.J. et al., "Oligonucleotides With Fluorescent Dyes at Opposite Ends Provide a Quenched Probe System Useful for Detecting PCR Product and Nucleic Acid Hybridization", Genome Research 4:357-362 (1995).

(Continued)

*Primary Examiner* — James Martinell
(74) *Attorney, Agent, or Firm* — Knobbe, Martens, Olson & Bear LLP

(57) ABSTRACT

The present invention relates generally to a method for assessing nucleic acid methylation, in particular DNA and RNA methylation. More particularly, the present invention relates to a method of either qualitatively or quantitatively assessing, with improved sensitivity, the cytosine methylation of partially methylated DNA or RNA. The method of the present invention is useful in a range of applications including, but not limited to, the diagnosis of conditions or monitoring of developmental phenotypes which are characterised by DNA or RNA methylation changes.

31 Claims, 3 Drawing Sheets

Specification includes a Sequence Listing.

(56) References Cited

OTHER PUBLICATIONS

Messing J., "New M13 Vectors for Cloning", Methods in Enzymology 101:20-78 (1983).
Mhlanga M.M. et al., "Using Molecular Beacons to Detect Single-Nucleotide Polymorphisms With Real-Time PCR", Methods 25:463-471 (2001).
Mitchell S M et al., "A Panel of Genes Mehtylated With High Frequency in Colorectal Cancer", BMC Cancer 14:54 (2014).
Narang S.A. et al., "Improved Phosphotriester Method for the Synthesis of Gene Fragments", Methods in Enzymology 68:90-98 (1979).
Nielsen P. et al., "Synthesis of 2'-O,3'-C-Linked Bicyclic Nucleotides and Bicyclic Oligonucleotides", J. Chem. Soc., Perkin Trans 1:3423-3433 (1997).
Orum H. et al., "Detection of the Factor V Leiden Mutation by Direct Allele-Specific Hybridization of PCR Amplicons to Photoimmobilized Locked Nucleic Acids", Clinical Chemistry 45(11):1898-1905 (1999).
Orum H. et al., "Single Base Pair Mutation Analysis by PNA Directed PCR Clamping", Nucleic Acids Research 21 (23):5332-5336 (1993).
Pedersen S.K. et al., "A Two-Gene Blood Test for Methylated DNA Sensitive for Colorectal Cancer", PLoS ONE 10(4):e0125041 (2015).
Santalucia Jr. J., "A Unified View of Polymer, Dumbbell, and Oligonucleotide DNA Nearest-Neighbor Thermodynamics", Proc. Natl. Acad. Sci. USA 95:1460-1465 (Feb. 1998).
Simeonov A. et al., "Single Nucleotide Polymorphism Genotyping Using Short, Fluorescently Labeled Locked Nucleic Acid (LNA) Probes and Fluorescence Polarization Detection", Nucleic Acids Research 30(17):e91 (2002).
Singh S.K. et al., "Universality of LNA-Mediated High-Affinity Nucleic Acid Recognition", Chem. Commun., pp. 1247-1248 (1998).
International Search Report dated Jan. 14, 2016 in International Application No. PCT/AU2015/050297.

* cited by examiner

FIGURE 2

Flow Chart of bisulfite-conversion and subsequent PCR amplification

SEQ ID1 (wildtype)    5' GACGACGCAC CCTCTCCGTG TCCCGCTCTG CGCGCCCCGC GCCCCCTCTG CGGGGCCCGC TCCCCGTACC GGAGCAGCGA TCCGGGAGGC GGCCGAGAGG TGCGC 3'

Watson ("top") strand    5' GACGAGGCAC CCTCTCCGTG TCCCGCTCTG CGCGCCCCGC GCCCCCTCTG CGGGGCCCGC TCCCCGTACC GGAGCAGCGA TCCGGGAGGC GGCCGAGAGG TGCGC 3'
Crick ("bottom") strand  3' CTGCTCCGTG GGAGAGGCAC AGGGGCGAGAC GCGCGGGGCG GGGGGAGAC GCCCCGGGCG AGGGGCATGG CCTCGTCGCT AGGCCCTCCG CCGGCTCTCC ACGCG 5'
(methylated cytosine in bold)

bisulfite
conversion
↓ bis-Watson strand    5' GACGACGUAU UUTUCGTG TUUCGUTUTG CGUUTTUTG CGUUGUUUG TUUCGUTAUC GGAGUAGCGA TUCGGGAGGC GGUCGAGAGG TGCGC 3'
bis-Crick strand    3' UTGCTGCGTG GGAGAGGCAU AGGGCGAAGAU GCGCGGGGCG CUTUGUGCT AGGCUTUUG CUUGUGUGCT AGGCUUUUG CUGGCUTUUG AUGCG 5'
(unmethylated cytosine will be converted to uracil)

1st round PCR (only SEQ ID NO:4 Reverse Primer can bind)

bis-Watson strand    5' GACGACGUAU UUTUCGTG TUUCGUTUTG CGUUTTUTG CGUUGUUUG TUUCGUTAUC GGAGUAGCGA TUCGGGAGGC GGUCGAGAGG TGCGC 3'
SEQ ID NO:4                                                                                                   3' G CCAGCUCTCC ACGCG 5'

↓ DNA synthesis bis-Watson strand    5' GACGACGUAU UUTUCGTG TUUCGUTUTG CGUUGUUUG TGUUCGUTG CGUUGUUUG TUUCGUTAUC GGAGUAGCGA TUCGGGAGGC GGUCGAGAGG TGCGC 3'
bis-Watson antisense  3' CTGCTGCATA AAAAAGGCAC AAAAGCAAAAC GCAAAAAAAAC GCGCAAAGCA CCTCATCGCT AAGCCCTCCG CCAGCCTCCG ACGCG 5'
↓

FIGURE 2 (continued)

2<sup>nd</sup> round PCR (SEQ ID3, 4, and 5-12 can bind depending on methylation status)

```
bis-Watson strand    5' GAGGACGUAU UUUUUCGUC UUCCGUUUG CGUUUUUUG CGAAGAGGA UUCCGAGCC GGGCGAGAGG UGCCC 3'
SEQ ID NO:4                                                              3' G CCAGCTCTCC ACGCG 5'
          SEQ ID NO:3                          SEQ ID NO:5 5' FAM-TTTGTATC GGAGTAGCGA TTCGGGAGG-Quench 3'
bis-Watson antisense 3' CTGCTGCATA AAAAAGCAC AAAGCAAAAC GCAAAAAAAC GCTCATCGCT AAGCCCTCCG CCAGCTCTCC ACGCG 5'

↓ DNA synthesis results in double-stranded DNA and fluorescence from degraded probe (eg SEQ ID NO:5)
      The resulting top strand (bis-Watson sense strand) becomes SEQ ID NO:2.

bis-Watson sense     5' GACGAGTAT TTTTTCGTG TTCGG-TTTG CGTTTTTTG GGAGTAGCGA TTCGGGAGGC GGTCGAGAGG TGCGC 3'
SEQ ID NO:2
bis-Watson antisense 3' CTGCTGCATA AAAAAGCAC AAAGCAAAAC GCAAAAAAAC GCTCATCGCT AAGCCCTCCG CCAGCTCTCC ACGCG 5'

⇓

Further rounds of PCR (SEQ ID NOs 3, 4, and 5-12 can bind depending on methylation status)
```

METHOD FOR METHYLATION ANALYSIS

FIELD OF THE INVENTION

The present invention relates generally to a method for assessing nucleic acid methylation, in particular DNA and RNA methylation. More particularly, the present invention relates to a method of either qualitatively or quantitatively assessing, with improved sensitivity, the cytosine methylation of partially methylated DNA or RNA. The method of the present invention is useful in a range of applications including, but not limited to, the diagnosis of conditions or monitoring of developmental phenotypes which are characterised by DNA or RNA methylation changes.

INCORPORATION BY REFERENCE OF SEQUENCE LISTING

The Sequence Listing in an ASCII text file, named 34406_Sequence_Listing.txt of 23 KB, created on Dec. 1, 2016, and submitted to the United States Patent and Trademark Office via EFS-Web, is incorporated herein by reference.

BACKGROUND OF THE INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Bibliographic details of the publications referred to by author in this specification are collected alphabetically at the end of the description.

DNA methylation is one of the most intensely studied epigenetic modifications in mammals and refers to the addition of a methyl (CH3) group to a cytosine (C) or adenine nucleotides. This methyl group may be added to the fifth carbon atom of the cytosine base or the sixth nitrogen atom of the adenine base.

DNA methylation plays a role in gene regulation in animal cells. Not only is there a correlation between active gene transcription and hypo-methylation, but also transfection experiments show that the presence of methyl moieties inhibits gene expression in vivo. Furthermore, gene activation can be induced by treatment of cells with 5-azacytidine, a potent demethylating agent. Methylation appears to influence gene expression by affecting the interactions of DNA with both chromatin proteins and specific transcription factors. Although methylation patterns are very stable in somatic cells, the early embryo is characterised by large alterations in DNA methylation.

DNA methylation is therefore vital to healthy growth and development and is linked to various processes such as genomic imprinting, carcinogenesis and the suppression of repetitive elements. It also enables the expression of retroviral genes to be suppressed, along with other potentially dangerous sequences of DNA that have entered and may damage the host. In addition, DNA methylation plays an important role in the development of cancer and is a key regulator of gene transcription. Studies have shown that genes with a promoter region that contains a high concentration of 5-methylcytosine are transcriptionally silent.

Between 60% and 90% of all CpGs are methylated in mammals. Methylated cytosine residues spontaneously deaminate to form T residues over time; hence methylated CpG dinucleotides steadily deaminate to TpG dinucleotides, which is evidenced by the under-representation of CpG dinucleotides in the human genome (they occur at only 21% of the expected frequency). CpGs are often grouped in clusters called CpG islands, which are typically present in the 5' regulatory regions of many genes.

With growing evidence of the diagnostic utility of monitoring DNA methylation levels, means for reliably and accurately assessing DNA methylation is becoming increasingly important. Currently, methylation-specific PCR is a commonly used method for detecting methylated DNA in bisulphite-converted DNA. In this method, PCR oligonucleotide primers interrogate methylated cytosine residues in cytosine-phosphodiester-guanidine [CpG] sites. MethyLight PCR is a real-time PCR variation which, in addition to methylation specific primers, also uses a 5'-3' hydrolysis probe for interrogation of methylated CpG sites, thereby enabling quantification.

More recently, RNA has also been shown to contain methylated cytosine residues, as well as methylated adenine residues (Liu and Jia, 2014; *J Genet Genomics.* 41(1):21-33). Although the biological role of methylated cytosine in RNA is unclear, it is an abundant modification in mRNA, suggesting that it might be an RNA epigenetic marker. In work leading up to the present invention it has been determined that in the context of some diagnostic applications which are based on screening for a change in the methylation pattern of a given gene, the accuracy of the diagnostic result is significantly reduced where partial methylation exists across a CpG-rich target region of interest. This is due to the fact that a commonly used methylation specific PCR is based on oligonucleotides requiring all targeted CpG sites to be methylated. For example, a probe-based method, such as MethyLight, requires that all interrogated CpG sites are methylated in order for the probe to hybridise for the successful detection of a given methylated DNA or RNA target. Where one or more CpG sites are not methylated, the probe cannot bind, thereby skewing the results that are obtained and significantly reducing diagnostic sensitivity. For example, in one aspect of the present invention, it has been determined that methylation of the promoter region of the IKZF1 gene occurs with high frequency in colorectal cancer tissues and that the detection of methylated IKZF1 DNA in cell free DNA which is present in the blood indicates the presence of colorectal cancer. Further studies, however, have demonstrated that certain colorectal cancer patients contain circulating tumour-derived IKZF1 DNA where not all the targeted CpG sites are methylated. Thus, an oligonucleotide, such as a hydrolysis probe designed to span methylated CpG sites within the IKZF1 DNA, does not allow detection of partially-methylated IKZF1 DNA. Accordingly colorectal cancer patients with a partially methylated IKZF1 DNA will consequently be reported as negative.

Accordingly, there is a need to develop improved methods that enable accurate and sensitive detection of DNA or RNA methylation, thereby improving the sensitivity of the applications for DNA or RNA methylation analysis, such as the diagnosis or monitoring of neoplastic disease. In still further work, it has been determined that the problem of false negative results can be reduced or eliminated via the use of one or more probes and/or primers which are designed to collectively detect at least two differing methylation patterns within a given DNA or RNA region of interest.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

The subject specification contains nucleotide sequence information prepared using the programme PatentIn Version 3.5, presented herein after the bibliography. Each nucleotide sequence is identified in the sequence listing by the numeric indicator <210> followed by the sequence identifier (e.g. <210>1, <210>2, etc). The length, type of sequence (DNA, etc) and source organism for each sequence is indicated by information provided in the numeric indicator fields <211>, <212> and <213>, respectively. Nucleotide sequences referred to in the specification are identified by the indicator SEQ ID NO: followed by the sequence identifier (e.g. SEQ ID NO:1, SEQ ID NO:2, etc.). The sequence identifier referred to in the specification correlates to the information provided in numeric indicator field <400> in the sequence listing, which is followed by the sequence identifier (e.g. <400>1, <400>2, etc). That is SEQ ID NO:1 as detailed in the specification correlates to the sequence indicated as <400>1 in the sequence listing.

One aspect of the present invention is directed to a method for detecting the cytosine methylation of a nucleic acid target of interest, which nucleic acid target may be characterised by a region of partial cytosine methylation, said method comprising:
 (i) contacting a nucleic acid sample with an agent which modifies unmethylated cytosine residues;
 (ii) contacting a DNA form of the nucleic acid sample of step (i) with:
  (a) forward and reverse primers designed to amplify one or more fully or partially methylated forms of the modified region of partial cytosine methylation; and
  (b) one or more probes directed to said region of partial cytosine methylation wherein said one or more probes are capable of collectively hybridising to at least two differing methylation patterns at said region and wherein said probe incorporates a detection means;
 (iii) amplifying the DNA sample of step (ii) wherein the extension of said primers along said target of interest effects the detection of said hybridised probe; and
 (iv) qualitatively or quantitatively analysing the detection output of step (iii).

In another aspect the present invention is directed to a method for detecting the cytosine methylation of a DNA or RNA target of interest, which DNA or RNA target may be characterised by a region of partial cytosine methylation, said method comprising:
 (i) contacting a DNA or RNA sample with an agent which modifies unmethylated cytosine residues;
 (ii) contacting a DNA form of the sample of step (i) with:
  (a) forward and reverse primers designed to amplify one or more fully or partially methylated forms of the modified region of partial cytosine methylation; and
  (b) one or more probes directed to said region of partial cytosine methylation wherein said one or more probes are capable of collectively hybridising to at least two differing methylation patterns at said region and wherein said probe incorporates a detection means;
 (iii) amplifying the DNA sample of step (ii) wherein the extension of said primers along said target of interest effects the detection of said hybridised probe; and
 (iv) qualitatively or quantitatively analysing the detection output of step (iii).

In yet another aspect there is provided a method for detecting the cytosine methylation of a gene target, which gene target may be characterised by a region of partial cytosine methylation, said method comprising:
 (i) contacting a nucleic acid sample with an agent which modifies unmethylated cytosine residues;
 (ii) contacting a DNA form of the nucleic acid sample of step (i) with:
  (a) forward and reverse primers designed to amplify one or more fully or partially methylated forms of the modified gene region of partial cytosine methylation; and
  (b) one or more probes directed to said region of partial cytosine methylation wherein said one or more probes are capable of collectively hybridising to at least two differing methylation patterns at said region, and wherein said probe incorporates a detection means;
 (iii) amplifying the DNA sample of step (ii) wherein the extension of said primers along said gene target effects the detection of said hybridised probe; and
 (iv) qualitatively or quantitatively analysing the detection output of step (iii).

In still another aspect there is provided a method for detecting the cytosine methylation of the gene BCAT1, IKZF1, IRF4, GRASP, CAHM, SOX21, SLC6A15, NPY, ST8SIA1, ZSCAN18, COL4A2, DLX5, FGF5, FOXF1, FOXI2 or SDC2, which gene may be characterised by a region of partial cytosine methylation, said method comprising:
 (i) contacting a DNA sample with an agent which modifies unmethylated cytosine residues;
 (ii) contacting the DNA sample of step (i) with:
  (a) forward and reverse primers designed to amplify one or more fully or partially methylated forms of the modified gene; and
  (b) one or more probes directed to said region of partial methylation wherein said one or more probes are capable of collectively hybridising to at least two differing methylation patterns at said region, and wherein said probe incorporates a detection means;
 (iii) amplifying the DNA sample of step (ii) wherein the extension of said primers along said gene effects the detection of said hybridised probe; and;
 (iv) qualitatively or quantitatively analysing the detection output of step (iii).

In yet another aspect, there is provided a method for detecting the cytosine methylation of a nucleic acid target of interest, which nucleic acid target may be characterised by a region of partial cytosine methylation, said method comprising:

(i) contacting a nucleic acid sample with a bisulfite agent to convert unmethylated cytosine residues to uracil;

(ii) contacting a DNA form of the nucleic acid sample of step (i) with:

(a) forward and reverse designed to amplify one or more fully or partially methylated forms of the modified region of partial cytosine methylation; and (b) one or more probes directed to said region of partial methylation wherein said one or more probes are capable of collectively hybridise to at least two differing methylation patterns at said region, and wherein said probe incorporates a detection means;

(iii) amplifying the DNA sample of step (ii) wherein the extension of said primers along said DNA target of interest effects the detection of said hybridised probe; and (iv) qualitatively or quantitatively analysing the detection output of step (iii).

In still yet another aspect there is provided a method for detecting the cytosine methylation of a nucleic acid target of interest, which nucleic acid target may be characterised by a region of partial cytosine methylation, said method comprising:

(i) contacting a nucleic acid sample with an agent which modifies unmethylated cytosine residues;

(ii) contacting a DNA form of the sample of step (i) with:

(a) methylation specific forward and reverse primers designed to amplify one or more fully or partially methylated forms of the modified region of partial cytosine methylation; and (b) one or more probes directed to said region of partial methylation wherein said one or more probes collectively hybridise to at least two differing methylation patterns at said region, and wherein said probe incorporates a detection means;

(iii) amplifying the DNA sample of step (ii) wherein the extension of said primers along said target of interest effects the detection of said hybridised probe; and (iv) qualitatively or quantitatively analysing the detection output of step (iii).

In a further aspect, there is provided a method for detecting the cytosine methylation of a nucleic acid target of interest, which nucleic acid target may be characterised by a region of partial cytosine methylation, said method comprising:

(i) contacting a nucleic acid sample with a bisulfite agent which converts unmethylated cytosine residues to uracil;

(ii) contacting a DNA form of the sample of step (i) with:

(a) methylation-specific forward and reverse primers designed to amplify one or more fully or partially methylated forms of the modified region of partial cytosine methylation; and (b) one or more hydrolysis probes directed to said region of partial cytosine methylation wherein said one or more probes collectively hybridise to at least two differing methylation patterns at said region;

(iii) amplifying the sample of step (ii) wherein the extension of said primers along said DNA target of interest effects the detection of said hybridised probe; and (iv) qualitatively or quantitatively analysing the detection output of step (iii).

In another further aspect the present invention is directed to a method for detecting the cytosine methylation of a nucleic acid target of interest, which nucleic acid target may be characterised by a region of partial cytosine methylation, said method comprising:

(i) contacting a nucleic acid sample with an agent which modifies unmethylated cytosine residues;

(ii) contacting a DNA form of the sample of step (i) with:

(a) forward and reverse primers designed to amplify one or more fully or partially methylated forms of the modified region of partial cytosine methylation; and (b) one or more probes directed to said region of partial cytosine methylation wherein said one or more probes collectively hybridise to all full and partial methylation patterns at said region and wherein said probe incorporates a detection means;

(iii) amplifying the DNA sample of step (ii) wherein the extension of said primers along said target of interest effects the detection of said hybridised probe; and (iv) qualitatively or quantitatively analysing the detection output of step (iii).

In still another aspect, there is provided a method for detecting the cytosine methylation of a gene target, which gene target may be characterised by a region of partial cytosine methylation, said method comprising:

(i) contacting a DNA sample with sodium bisulfite to convert unmethylated cytosine residues to uracil;

(ii) contacting the DNA sample of step (i) with:

(a) methylation specific forward and reverse primers designed to amplify one or more fully or partially methylated forms of the modified gene; and (b) one or more hydrolysis probes directed to said region of partial cytosine methylation wherein said one or more probes collectively hybridise to at least two regions differing methylation patterns at said region;

(iii) amplifying the DNA sample of step (ii) wherein the extension of said primers along said DNA target of interest effects the detection of said hybridised probe; and (iv) qualitatively or quantitatively analysing the detection output of step (iii).

In yet another aspect the present invention is directed to a method for diagnosing or monitoring a condition in a patient which condition is characterised by modulation of the cytosine methylation of a DNA or RNA target and which DNA or RNA target is characterised by a region of partial methylation, said method comprising:

(i) contacting a nucleic acid sample from said patient with an agent which modifies unmethylated cytosine residues;

(ii) contacting the DNA form of the sample of step (i) with:

(a) forward and reverse primers designed to amplify one or more fully or partially methylated forms of the modified gene; and (b) one or more probes directed to said region of partial cytosine methylation wherein said one or more probes collectively hybridise to at least two differing methylation patterns at said region and wherein said probe incorporates a detection means;

(iii) amplifying the DNA sample of step (ii) wherein the extension of said primers along said target of interest effects the detection of said hybridised probe; and (iv) qualitatively or quantitatively analysing the detection output of step (iii).

Figure 1:
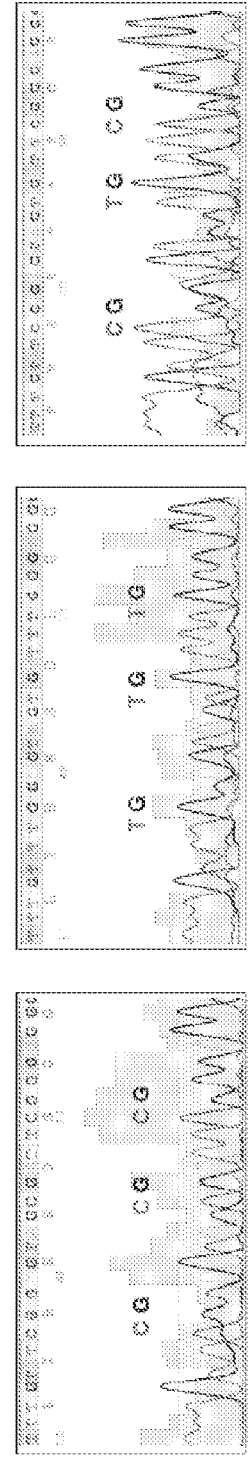
FIG. 1A provides examples of the partially methylated forms of a targeted IKZF1 region residing in Chr7.

50304271-50304365. Top line: reference fully methylated IZKF1 target sequence (after bisulfite-conversion and PCR amplification), with methylated cytosines highlighted in red. Positions of forward primer (SEQ ID:3), reverse primer (SEQ ID:4) and the probe requiring three fully methylated CpG sites are indicated. Identified partially methylated target sequences are shown below with green T's.

FIG. 1B is a representation of IKZF1 sample sequence traces identified in bisulphite converted DNA extracted from three clinical plasma samples using a IKZF1 methylation specific PCR (methylation specific primers). The three traces exemplify the existence of fully methylated IKZF1 (left panel), fully unmethylated IKZF1 (middle panel) and partially methylated IKZF1 (right panel). Peaks are colour-coded for the base being detected (red=T; black=G; green=A; blue=C). Positions of methylated CG bases under the probe are shown "CG" above those peaks; unmethylated CGs that convert to TGs after bisulphite conversion and PCR amplification are shown "TG".

FIG. 2 is a flow chart detailing bisulfite-conversion and subsequent PCR amplification.

DETAILED DESCRIPTION OF THE INVENTION

The present invention is predicated, in part, on the determination that the sensitivity of a quantitative PCR methylation analysis of a DNA or RNA sample which exhibits partial cytosine methylation can be significantly improved if the amplification reaction is designed with one or more detection probes or primers which are designed to collectively hybridise to at least two, but preferably all, of the potential methylation patterns of a DNA region of interest. The development of this method has been necessitated due to the surprising determination that the existence of partial methylation significantly reduces the sensitivity of a quantitative PCR-based methylation-detection assay, due to the fact that hydrolysis probes and primers directed to a methylated DNA region of interest will only hybridise to the amplified, bisulfite converted fully-methylated form of the DNA and not to the amplified, bisulfite-converted partially methylated forms of the DNA, despite the fact that the probe or primer otherwise exhibits a high level of sequence similarity. In fact, some diagnostic assays have, to date, been designed to detect only fully methylated forms of DNA, in light of the view that detecting partially methylated forms of DNA were thought to obscure the specificity of a diagnostic assay. However, it has now been determined that some diagnostic methylated gene markers, such as the colorectal cancer marker IKZF1, in fact exhibit partially methylated forms. Such forms are not detected by traditional quantitative PCR technology and they can be of sufficient proportions that the results obtained using the prior art technology are of reduced sensitivity.

The development of the method of the present invention has now enabled the routine application of methylation specific amplification assays which exhibit significantly higher sensitivity than has been previously attainable. More specifically, it has been determined that the use of either a heterogenous pool of probes or primers directed to the range of potential partial methylation patterns of the region of interest, or the use of a probe or primer which is promiscuous in its hybridisation functionality in that it is capable of hybridising to two or more differing methylation patterns, can efficiently detect both the amplified fully and partially methylated DNA or RNA molecules present in a sample, thereby improving the sensitivity of the test. In the context of cancer diagnosis, false negative results, arising from the use of prior art methods that cannot detect partial methylation, can have extremely serious consequences for a patient. Accordingly, the method of the present invention provides a simple but robust means of ensuring a high level of sensitivity when assessing DNA methylation.

Accordingly, one aspect of the present invention is directed to a method for detecting the cytosine methylation of a nucleic acid target of interest, which nucleic acid target may be characterised by a region of partial cytosine methylation, said method comprising:
 (i) contacting a nucleic acid sample with an agent which modifies unmethylated cytosine residues;
 (ii) contacting a DNA form of the nucleic acid sample of step (i) with:
  (a) forward and reverse primers designed to amplify one or more fully or partially methylated forms of the modified region of partial cytosine methylation; and
  (b) one or more probes directed to said region of partial cytosine methylation wherein said one or more probes are capable of collectively hybridising to at least two differing methylation patterns at said region and wherein said probe incorporates a detection means;
 (iii) amplifying the DNA sample of step (ii) wherein the extension of said primers along said target of interest effects the detection of said hybridised probe; and
 (iv) qualitatively or quantitatively analysing the detection output of step (iii).

Reference to a "nucleic acid target of interest" should be understood as a reference to any region or form of DNA or RNA, the methylation status of which is sought to be analysed. This may be, for example, a gene, part of a gene, an intergenic region or a promoter. To this end, reference to "gene" should be understood as a reference to a DNA or RNA molecule that codes for a protein product, whether that be a full length protein or a protein fragment. It should be understood, however, that there are some genes that have been identified which are not known to necessarily produce a protein product. Reference to "gene" herein should therefore be understood to include reference to both types of genes. In terms of genomic DNA or the RNA transcribed therefrom, the gene will generally be expected to include both intronic and exonic regions. The subject nucleic acid region of interest may also be a portion of genomic DNA which is not known to be associated with any specific gene (such as the commonly termed "junk" DNA regions). The nucleic acid target of interest may also be any region of genomic DNA (or RNA transcription product) produced by recombination, either between 2 regions of genomic DNA or 1 region of genomic DNA and a region of foreign DNA such as a virus or an introduced sequence. The DNA that is the subject of analysis need not necessarily be genomic DNA, although it is generally understood that recombinantly expressed DNA, such as cDNA, is not methylated. Nevertheless, the present invention should be understood to extend to the analysis of any source or form of DNA or RNA which may be methylated. For example, in relation to RNA, one might analyse primary RNA, mRNA, tRNA, rRNA, tmRNA, snRNA, snoRNA, miRNA, non-coding RNA or viral RNA.

Accordingly, the present invention is more particularly directed to a method for detecting the cytosine methylation of a DNA or RNA target of interest, which DNA or RNA target may be characterised by a region of partial cytosine methylation, said method comprising:

(i) contacting a DNA or RNA sample with an agent which modifies unmethylated cytosine residues;

(ii) contacting a DNA form of the sample of step (i) with:
   (a) forward and reverse primers designed to amplify one or more fully or partially methylated forms of the modified region of partial cytosine methylation; and
   (b) one or more probes directed to said region of partial cytosine methylation wherein said one or more probes are capable of collectively hybridising to at least two differing methylation patterns at said region and wherein said probe incorporates a detection means;

(iii) amplifying the DNA sample of step (ii) wherein the extension of said primers along said target of interest effects the detection of said hybridised probe; and (iv) qualitatively or quantitatively analysing the detection output of step (iii).

Without limiting the present invention to any one theory or mode of action, RNA methylation occurs in many different RNA species including tRNA, rRNA, mRNA, tmRNA, snRNA, snoRNA, miRNA non-coding RNA, and viral RNA. Different catalytic strategies are employed for RNA methylation by a variety of RNA-methyltransferases. As a post-translational modification, RNA methylation plays a significant role as an epigenetic mechanism. N6-methyladenosine ($m^6A$) is the most common and abundant methylation modification in RNA molecules present in eukaryotes, although 5-methylcytosine (5-mC) also commonly occurs in various RNA molecules. Recent data suggest that $m^6A$ and 5-mC RNA methylation affect the regulation of various biological processes, such as RNA stability and mRNA translation, and that abnormal RNA methylation contributes to the etiology of human diseases. Although the biological role of methylated cytosine in RNA is not fully understood, it is an abundant modification in mRNA.

Still without limiting the present invention in any way, DNA methylation is universal in bacteria, plants, and animals. DNA methylation is a type of chemical modification of DNA that is stable over rounds of cell division but does not involve changes in the underlying DNA sequence of the organism. Chromatin and DNA modifications are two important features of epigenetics and play a role in the process of cellular differentiation, allowing cells to stably maintain different characteristics despite containing the same genomic material. In eukaryotic organisms DNA methylation occurs only at the number 5 carbon of the cytosine pyrimidine ring. In mammals, DNA methylation occurs mostly at the number 5 carbon of the cytosine of a CpG dinucleotide. CpG dinucleotides comprise approximately 1% of the human genome.

70-80% of all CpGs are methylated. CpGs may be grouped in clusters called "CpG islands" that are typically present in the 5'-end of regulatory regions of many genes. In many disease processes such as cancer, gene promoters and/or CpG islands acquire abnormal hypermethylation, which is associated with heritable transcriptional silencing. DNA methylation may impact the transcription of genes in two ways. First, the methylation of DNA may itself physically impede the binding of transcriptional proteins to the gene, thus blocking transcription. Second, methylated DNA may be bound by proteins known as Methyl-CpG-binding domain proteins (MBDs). MBD proteins then recruit additional proteins to the locus, such as histone deacetylases and other chromatin remodelling proteins that can modify histones, thereby forming compact, inactive chromatin termed silent chromatin. This link between DNA methylation and chromatin structure is very important. In particular, loss of Methyl-CpG-binding Protein 2 (MeCP2) has been implicated in Rett syndrome and Methyl-CpG binding domain protein 2 (MBD2) mediates the transcriptional silencing of hypermethylated genes in cancer.

In humans, the process of DNA methylation is carried out by three enzymes, DNA methyltransferase 1, 3a and 3b (DNMT1, DNMT3a, DNMT3b). It is thought that DNMT3a and DNMT3b are the de novo methyltransferases that set up DNA methylation patterns early in development. DNMT1 is the proposed maintenance methyltransferase that is responsible for copying DNA methylation patterns to the daughter strands during DNA replication. DNMT3L is a protein that is homologous to the other DNMT3s but has no catalytic activity. Instead, DNMT3L assists the de novo methyltransferases by increasing their ability to bind to DNA and stimulating their activity. Finally, DNMT2 has been identified as an "enigmatic" DNA methyltransferase homolog, containing all 10 sequence motifs common to all DNA methyltransferases; however, DNMT2 may not methylate DNA but instead has been shown to methylate a small RNA.

The term "methylation" should therefore be understood to mean the presence of a methyl group added by the action of a DNA methyl transferase enzyme to cytosine or adenosine bases in a region of nucleic acid, e.g. genomic DNA or RNA.

In one embodiment, said nucleic acid target of interest is a DNA or RNA gene or gene region; such as the promoter region. Reference to "gene target" should therefore be understood as a reference to a gene or region of a gene in respect of which the methylation is to be interrogated.

Reference to a "region of a gene" should be understood as a reference to any stretch of DNA or RNA which corresponds to part of a gene but not the entire gene. For example, the DNA which is analysed by the method of a present invention may be fragmented, such as during its isolation, or it may have been cleaved as a preliminary step prior to analysis by the method of the present invention. For example, GlaI cleaves at specific sites if IKZF1 is methylated. The generated GlaI fragments can then be amplified using appropriate primers and the degenerate probes of the present invention used to assess methylation.

According to this embodiment there is provided a method for detecting the cytosine methylation of a gene target, which gene target may be characterised by a region of partial cytosine methylation, said method comprising:

(i) contacting a nucleic acid sample with an agent which modifies unmethylated cytosine residues;

(ii) contacting a DNA form of the nucleic acid sample of step (i), which nucleic acid sample is in the form of DNA with:
   (a) forward and reverse primers designed to amplify one or more fully or partially methylated forms of the modified gene region of partial cytosine methylation; and
   (b) one or more probes directed to said region of partial cytosine methylation wherein said one or more probes are capable of collectively hybridising to at least two differing methylation patterns at said region and wherein said probe incorporates a detection means;

(iii) amplifying the DNA sample of step (ii) wherein the extension of said primers along said gene target effects the detection of said hybridised probe; and (iv) qualitatively or quantitatively analysing the detection output of step (iii).

In another embodiment, said gene or gene region is a mammalian gene or gene region.

In a further embodiment, said gene is a large intestine neoplasm marker and, more particularly, BCAT1, IKZF1, CAHM, GRASP, IRF4, SOX21, SLC6A15, NPY, ST8SIA1, ZSCAN18, COL4A2, DLX5, FGF5, FOXF1, FOXI2 or SDC2.

These genes are specified herein by reference to both gene name and a set of human chromosomal coordinates. Both the gene names and the chromosomal coordinates would be well known to, and understood by, the person of skill in the art. In general, a gene can be routinely identified by reference to its name, via which both its sequences and chromosomal location can be routinely obtained, or by reference to its chromosomal coordinates, via which both the gene name and its sequence can also be routinely obtained.

Reference to "genes" should be understood as a reference to all forms of these molecules and to fragments or variants thereof. As would be appreciated by the person skilled in the art, some genes are known to exhibit allelic variation between individuals or single nucleotide polymorphisms. Such variations include SNPs, insertions and deletions of varying size and simple sequence repeats, such as dinucleotide and trinucleotide repeats. Variants include nucleic acid sequences from the same region sharing at least 90%, 95%, 98%, 99% sequence identity i.e. having one or more deletions, additions, substitutions, inverted sequences etc. relative to the genes described herein. Accordingly, the present invention should be understood to extend to such variants which, in terms of the present diagnostic applications, achieve the same outcome despite the fact that minor genetic variations between the actual nucleic acid sequences may exist between individuals. The present invention should therefore be understood to extend to all forms of DNA or RNA that arise from any other mutation, polymorphic or allelic variation.

The GRCh38/hg38 chromosomal coordinates corresponding to the genes detailed above are as follows:
(1) BCAT1: chr12: 24810024-24949459
(2) IKZF1: chr7:50304083-50405100
(3) IRF4: chr6: 391739-411443
(4) GRASP: chr12: 52006945-52015889
(5) CAHM: chr6: 163413065-163413950
(6) SOX21: chr13:94709625-94712135
(7) SLC6A15: chr12: 84859488-84912829
(8) NPY: chr7: 24284188-24291865
(9) ST8SIA1: chr12: 22193391-22334714
(10) ZSCAN18: chr19: 58083842-58098363
(11) COL4A2: chr13: 110307284-110513026
(12) DLX5: chr7: 97020390-97024831
(13) FGF5: chr4: 80266588-80291017
(14) FOXF1: chr16: 86510527-86514464
(15) FOXI2: chr10: 127737274-127741186
(16) SDC2: chr8: 96493654-96611809

Reference to these genes should be understood to include 5 kb upstream of the transcription start site of each of these genes. Without limiting the present invention to any one theory or mode of action, IKZF1 is generally understood to span chr7:50304782-50405100 (Assembly GRCh38/hg38). This runs from the transcription start site to the polyadenylation site. However, the IKZF1 gene has a further 5' transcription start site, the coordinates of which, including this start site, are Chr7:50304083-50405100. If the upstream CpG Island is also included then the coordinates are 50303300-50405100.

As will be discussed in more detail hereafter, the method of the present invention can be applied to screening for the methylation of one gene or else it can be adapted to screen a given biological sample for the methylation of more than one gene either via amplification of separate aliquots of DNA or RNA from the original biological sample or in the context of a single aliquot which is amplified using a multiplexed amplification method.

As detailed hereinbefore, the method of the present invention is predicated on the development of a method for detecting a partially methylated DNA or RNA target of interest. Reference to "partial methylation" is a reference to a CpG-containing DNA target in which one or more cytosines that are normally methylated in the fully methylated form of that DNA target are not methylated in the partially methylated form. For example, and in one embodiment of the present invention, the fully methylated form of the gene IKZF1 at Chr7:50304323-50304349 is:

CCTGTAC $^m$CGGAGCAG $^m$CGATC $^m$CGGGAGG where $^mC$ represents a methylated cytosine and C represents an unmethylated cytosine.
The range of potential partially methylated forms of this region of the IKZF1 DNA sequence are:

```
                                            (SEQ ID NO 80)
    CCTGTACCGGAGCAG ᵐCGATC ᵐCGGGAGG (SEQ ID NO 81)
    CCTGTAC ᵐCGGAGCAGCGATC ᵐCGGGAGG (SEQ ID NO 82)
    CCTGTAC ᵐCGGAGCAG ᵐCGATCCGGGAGG (SEQ ID NO 83)
    CCTGTACCGGAGCAGCGATC ᵐCGGGAGG (SEQ ID NO 84)
    CCTGTACCGGAGCAG ᵐCGATCCGGGAGG (SEQ ID NO 85)
    CCTGTAC ᵐCGGAGCAGCGATCCGGGAGG (SEQ ID NO 86)
    CCTGTACCGGAGCAGCGATCCGGGAGG.
```

It should be understood that any given biological sample may comprise all or only some of these partially methylated forms of IKZF1. Still further, in the context of the IKZF1 embodiment, the above-identified sequences represent three potential partially methylated forms of the Chr7:50304323-50304349 region of the IKZF1 gene. However, it should also be understood that other regions of the IKZF1 gene may exhibit partial methylation, such as other CpG islands residing in the IKZF1 gene (chr7:50303300-50304923 and chr7: 50399869-50400702). A corresponding meaning for "partial methylation" should be understood to apply to any target of interest, such as any gene, transcription product or other DNA or RNA target, such as mRNA. It would be appreciated by the person of skill in the art that in terms of performing the method of the present invention, the region of DNA or RNA that is selected for analysis will likely reflect a discrete region of the DNA or RNA target which exhibits partial methylation. It is not the case that every region of partial methylation of the DNA or RNA target need necessarily be analysed.

The nucleic acid target that is interrogated by the method of the present invention is one that "may" be characterised by a region of partial methylation. Reference to "may" should be understood to mean that the nucleic acid sample that is the subject of testing may or may not actually include partially methylated sequences. Without limiting the present invention to any one theory or mode of action, the fact that a given gene may exhibit partially methylated variations does not mean that in every biological sample which is analysed one will observe the existence of one or more partially methylated forms. Rather, the existence and extent of partial methylation can depend on factors such as the nature of the sample being analysed, the nature of the disease condition in issue, the severity of disease stage and the like. However, there is no need for the skilled person to necessarily determine in advance whether or not partially methylated forms of the gene in issue are present in the nucleic acid sample being tested. Rather, one may simply apply the method of the present invention to any sample since the sequence to which the probe is directed is known and one can therefore generate a pool of probes to hybridise to every permutation of partial methylation that is theoretically possible. In respect of whether the DNA sample being tested is actually fully methylated or partially methylated (and irrespective of the range of partially methylated forms which may be present) provided that sufficient primer and probe quantities are used, the presence of excess primer or probes that have not hybridised will not affect the results obtained from the primers and probes that have hybridised and are measured.

In another embodiment of the present invention, the DNA target is BCAT1, IKZF1, IRF4, GRASP, CAHM, SOX21, SLC6A15, NPY, ST8SIA1, ZSCAN18, COL4A2, DLX5, FGF5, FOXF1, FOXI2 or SDC2.

According to this embodiment there is provided a method for detecting the cytosine methylation of the gene BCAT1, IKZF1, IRF4, GRASP, CAHM, SOX21, SLC6A15, NPY, ST8SIA1, ZSCAN18, COL4A2, DLX5, FGF5, FOXF1, FOXI2 or SDC2, which gene may be characterised by a region of partial cytosine methylation, said method comprising:
  (i) contacting a DNA sample with an agent which modifies unmethylated cytosine residues;
  (ii) contacting the DNA sample of step (i) with:
    (a) forward and reverse primers designed to amplify one or more fully or partially methylated forms of the modified gene; and
    (b) one or more probes directed to said region of partial methylation wherein said one or more probes are capable of collectively hybridising to at least two differing methylation patterns at said region, and wherein said probe incorporates a detection means;
  (iii) amplifying the DNA sample of step (ii) wherein the extension of said primers along said gene effects the detection of said hybridised probe; and;
  (iv) qualitatively or quantitatively analysing the detection output of step (iii).

In another embodiment, said gene is IKZF1.

The nucleic acid that is tested in accordance with the method of the present invention may be isolated from a biological sample. Reference to a "biological sample" should be understood as a reference to any sample of biological material derived from any source, such as animal, plant or bacterial, including but not limited to, cellular material, biofluids (e.g. blood, urine, saliva), faeces, tissue biopsy specimens, surgical specimens or fluid which has been introduced into the body and subsequently removed (such as, for example, the solution retrieved from an enema wash). The biological sample that is tested according to the method of the present invention may be tested directly or may require some form of treatment prior to testing. For example, a biopsy or surgical sample may require homogenisation prior to testing. Alternatively, a cell sample may require permeabilisation prior to testing. Further, to the extent that the biological sample is not in liquid form, (if such form is required for testing) it may require the addition of a reagent, such as a buffer, to mobilise the sample.

To the extent that the nucleic acid region of interest is present in a biological sample, the biological sample may be directly tested or else all or some of the nucleic acid present in the biological sample may be isolated prior to testing. In yet another example, the sample may be partially purified or otherwise enriched prior to analysis. For example, to the extent that a biological sample comprises a very diverse cell population, it may be desirable to enrich for a sub-population of particular interest. It is within the scope of the present invention for the target biological sample or molecules derived therefrom to be treated prior to testing, for example, inactivation of live virus. It should also be understood that the biological sample may be freshly harvested or it may have been stored (for example by freezing) prior to testing or otherwise treated prior to testing (such as by undergoing culturing).

The choice of what type of sample is most suitable for testing in accordance with the method disclosed herein will be dependent on the nature of the situation. To the extent that one is screening for the onset or predisposition to the onset of a large intestine neoplasm, for example, said sample is preferably a faecal (stool) sample, enema wash, surgical resection, tissue biopsy or blood sample (e.g. whole blood, serum or plasma).

More preferably, said biological sample is a blood sample, biopsy sample or stool sample.

The method of the present invention provides a means of accurately qualitatively or quantitatively analysing the cytosine methylation characteristics of a nucleic acid target, such as DNA or RNA, via amplification-based methodology. By applying the method of the present invention, the results are not skewed by virtue of the potential existence of partial methylation in any given biological sample, specifically due to the generation of false negative results caused by the fact that the amplification primer or detection probe can only hybridise to a fully methylated nucleic acid sequence and not a corresponding partially methylated sequence. In terms of applying this method it should be appreciated by the person of skill in the art that any of the existing amplification methods which are designed to interrogate the methylation of a DNA sequence, via a combination of amplification and probing, can be adapted in accordance with the method of the present invention. For example, one can design an amplification method (such as PCR) that uses either methylation specific primers or non-methylation specific primers. In accordance with the exemplified embodiment, methylation specific primers are used (e.g. methylation-specific PCR). However, non-methylation specific primers could also be used, although in this case the methylation interrogation will rely solely on the results obtained from the use of the probes. Similarly, in terms of the probes that are used, the exemplified embodiment uses hydrolysis probes, which enable real-time PCR quantification to be achieved. However, even where such probes are used, it may be sufficient to qualitatively analyse the readout that is obtained. Alternatively, one may elect to use a probe that only provides a qualitative readout and does not enable quantitative analysis.

In a first step, the nucleic acid sample that is the subject of analysis is contacted with an agent to modify unmethylated cytosine residues. The term "modifies" as used herein means the conversion of an unmethylated cytosine to another nucleotide by an agent, said conversion distinguishing unmethylated from methylated cytosine in the original nucleic acid sample. Any suitable agent may be used. In one embodiment, the agent is one that converts unmethylated cytosine to uracil, such as sodium bisulfite. However, other equivalent modifying agents that selectively modify unmethylated cytosine, but not methylated cytosine, can be used in the method of the invention. For example, one can use any other suitable form of bisulfite, such as ammonium bisulfite. Sodium-bisulfite readily reacts with the 5, 6-double bond of cytosine, but not with methylated cytosine, to produce a sulfonated cytosine intermediate that undergoes deamination under alkaline or high temperature conditions to produce uracil. Because Taq polymerase recognises uracil as thymine and 5-methylcytosine (m5C) as cytosine, the sequential combination of sodium bisulfite treatment and PCR amplification results in the ultimate conversion of unmethylated cytosine residues to thymine (C→U→T) and methylated cytosine residues ("mC") to cytosine (mC-→mC→C). Thus, sodium-bisulfite treatment of genomic DNA creates methylation-dependent sequence differences by converting unmethylated cytosines to uracil. It should be understood that in terms of the hybridising of primers to the nucleic acid of step (i), the primers are designed to hybridise to the modified (eg. bisulfite-converted) DNA, or the DNA amplified therefrom.

According to this embodiment, there is provided a method for detecting the cytosine methylation of a nucleic acid target of interest, which nucleic acid target may be characterised by a region of partial cytosine methylation, said method comprising:

(i) contacting a nucleic acid sample with a bisulfite agent to convert unmethylated cytosine residues to uracil;

(ii) contacting a DNA form of the nucleic acid sample of step (i), with:

(a) forward and reverse primers designed to amplify one or more fully or partially methylated forms of the modified region of partial cytosine methylation; and (b) one or more probes directed to said region of partial methylation wherein said one or more probes are capable of collectively hybridise to at least two differing methylation patterns at said region, and wherein said probe incorporates a detection means;

(iii) amplifying the DNA sample of step (ii) wherein the extension of said primers along said target of interest effects the detection of said hybridised probe; and (iv) qualitatively or quantitatively analysing the detection output of step (iii).

In another embodiment, said bisulfite agent is a bisulfite salt, such as sodium bisulfite or ammonium bisulfite.

In still another embodiment said nucleic acid target is a gene and, more preferably, BCAT1, IKZF1, IRF4, GRASP or CAHM, SOX21, SLC6A15, NPY, ST8SIA1, ZSCAN18, COL4A2, DLX5, FGF5, FOXF1, FOXI2 or SDC2.

In yet another embodiment, said nucleic acid target is genomic IKZF1 DNA. Once the conversion of unmethylated cytosine residues has been effected, the sample is ready for amplification. Where the nucleic acid sample that is the subject of analysis is a DNA sample, such as a genomic DNA sample, the amplification reaction can be performed directly on the bisulfite-converted sample. However, where the nucleic acid sample of interest is an RNA sample, such as an mRNA sample, it is necessary that the RNA is converted to DNA prior to the amplification of step (ii). This can be done by any convenient method that would be well known to the person of skill in the art, such as RT-PCR. Without limiting the present invention to any one theory or mode of action, this can be accomplished in a "one-step" reaction (e.g., using Tth polymerase, which has both reverse-transcriptase and DNA polymerase activity) or a "two-step reaction", where one uses two separate enzymes such as reverse-transcriptase and a thermostable DNA polymerase. It would be understood by the skilled person that in the context of the "one-step" reaction, one may still perform this method in two stages. Generally a reverse transcription step can be performed at room temperature and thereafter a normal PCR step. In accordance with this embodiment one might typically design one method in which the RNA sample in issue is contacted with a suitable complementary primer(s), which may include random primers, an enzyme with reverse-transcriptase activity, deoxy-nucleotide triphosphates and suitable buffer and incubation conditions to produce complementary DNA (cDNA). Accordingly, reference to contacting a "DNA form of the nucleic acid sample of step (i)" should be understood as a reference to the fact that the nucleic acid sample which is subjected to amplification in step (ii) is in a DNA form. To this end, it should be understood that even where the nucleic acid of step (i) is originally a DNA sample, and could be immediately used in step (ii), it may nevertheless be desirable to amplify the sample, thereby increasing its quantity, prior to applying the amplification step (ii). Where the sample is RNA, it will be subjected to a step such as RT-PCR to convert that RNA into a DNA form prior to step (ii) amplification.

The amplification of step (ii) can be achieved using any one of a number of suitable techniques. For example, where more than one pair of forward/reverse primers are used, directed to targeting two or more separate gene or methylation regions, one may introduce all these primers to a single sample and amplify the sample using a multiplexed amplification technique. Alternatively, one may elect to divide the sample of step (i) into more than one aliquot wherein each aliquot is amplified using a separate pair of primers. It should also be understood that the skilled person may elect to adapt this method so as to use multiple sets of primers, directed to amplifying only one methylation region but where the multiple primers reflect the application of a nested PCR reaction.

Reference to a "primer" should be understood as a reference to any molecule comprising a sequence of nucleotides, or functional derivatives or analogues thereof, the function of which includes both annealing to a complementary DNA sequence which flanks the methylation region of interest and amplification of the DNA sequence downstream of the annealing region. It should be understood that the primer may comprise non-nucleic acid components. For example, the primer may also comprise a non-nucleic acid tag such as a fluorescent or enzymatic tag or some other non-nucleic acid component that facilitates the use or detection of the molecule. In another example, the primer may be a protein nucleic acid that comprises a peptide backbone exhibiting nucleic acid side chains. Preferably, said primer is a single stranded DNA oligonucleotide.

The design and synthesis of primers suitable for use in the present invention would be well known to those of skill in the art. In one embodiment, the subject primer is 4 to 60 nucleotides in length, in another embodiment 10 to 50 nucleotides in length, in yet another embodiment 15 to 45 nucleotides in length, and in still another embodiment 20 to 40 nucleotides in length.

In terms of the number of primers that are used in the method of the invention, this can be determined by the person of skill in the art. With regard to the total number of primers, the variables that require consideration are the size and number of nucleic acid regions that are being amplified and the distance between the sequences to which the primers hybridise. In order to amplify PCR fragments that are larger than about 1 kb, the primers can be designed to function in a nested PCR method and to hybridise at intervals of approximately 500 bases.

In one embodiment, the oligonucleotide primers are linear, single-stranded oligomeric deoxyribonucleic or ribonucleic acid molecules capable of sequence-specific hybridisation with complementary strands of nucleic acid. The primers are preferably DNA. The primers of the invention are of sufficient length to provide for specific and efficient initiation of polymerization (primer extension) during the amplification process. The exact length will depend on multiple factors including temperature (during amplification), buffer, and nucleotide composition. Preferably, the primers are single-stranded although double-stranded primers may be used if the strands are first separated. Primers may be prepared using any suitable method, such as conventional phosphotriester and phosphodiester methods or automated embodiments, which are commonly known in the art.

As used herein the specific primers are preferably designed to be substantially complementary to each strand of the genomic nucleic acid of interest. Typically, one primer is complementary to the negative (−) strand of the locus (the "lower" strand of a horizontally situated double-stranded DNA molecule) and the other is complementary to the positive (+) strand ("upper" strand). It should be understood that the method of the invention can be designed to amplify the relevant regions of either the sense strand or the anti-sense strand of the gene target of interest. Exemplification in this regard is provided herein in the context of IKZF1.

As detailed hereinbefore, the primers that are utilised in the method of the present invention may be any suitable primers that amplify the nucleic acid target of interest. For example, the primers may be methylation-specific primers or non-methylation specific primers. By "methylation-specific" primers is meant primers which can distinguish between methylated and non-methylated DNA, such as bisulfite converted methylated vs non-methylated DNA. Such methylation specific primers can be designed to distinguish between methylated and non-methylated DNA by, for example, hybridising with only unconverted 5-methylcytosines (i.e. the primer hybridises to bisulfite-converted methylated DNA) or, conversely, hybridising to thymines that are converted from unmethylated cytosines (i.e. the primer hybridises to bisulfite-converted unmethylated DNA). Methylation is thereby determined by the ability of the specific primer to achieve amplification. As would be appreciated by the person of skill in the art, in order to achieve methylation-specific discrimination the primers are preferably designed to overlap potential sites of DNA methylation (CpG dinucleotides) and to specifically distinguish modified unmethylated from methylated DNA. For example, the primers may be designed to overlap one to several CpG sequences, preferably one to five CpG sequences or one to four CpG sequences. In the context of the IKZF1 amplification exemplified herein, the forward and reverse primers are each designed to hybridise to a region of the IKZF1 sequence that comprises four CpG dinucleotides. In one preferred embodiment, the primers are methylation specific.

Accordingly, reference to said primers being "designed to amplify one or more fully or partially methylated forms of the region of partial cytosine methylation" should be understood to mean that the primers will enable amplification of either all or just some of the methylated forms of the subject region, these amplicons being thereafter interrogated by the probe. If the primer is non-methylation specific, it will amplify all of the forms of the subject region, irrespective of the existence or not of any degree of methylation. For example, the primers may be designed such that they hybridise to unmethylated DNA regions which are located upstream and downstream to the CpGs which form part of the region of partial cytosine methylation. In this situation, the primers will amplify this region of all the nucleic acid molecules present in the sample since the primers have been designed to hybridise to a DNA site which is unmethylated but which is located proximally to the methylated region of cytosines. In this case, the methylation specificity of the method will be provided only by the probes and it would be important to ensure that the pool of probes does not include a probe directed to a fully unmethylated form of the target region. In another embodiment one or more of the primers may be methylation specific and designed to hybridise to one or more of the cytosine residues which are fully methylated and which lie upstream and/or downstream of the region of partial methylation. By designing methylation-specific primers, methylation specific amplification can be achieved. In yet another example, one or both of the primers may be directed to the partially methylated residues themselves. In this situation, in order to achieve good sensitivity it is desirable to design a primer which hybridises promiscuously, or a pool of primers, which will hybridise to, and enable amplification of, as many different partially methylated forms of the DNA target as possible, thereby improving specificity. This may be achieved, for example, in the context of the application of a multiplexed assay. In terms of the design of either a suitable promiscuous primer or pool of primers, the description provided hereafter in relation to probe sequence design is also applicable to the design of these primers, both molecules being oligonucleotides which are designed to hybridise to a target DNA region.

It would be appreciated that where non-methylation specific primers are used, it is preferable that the panel of probes that is utilised does not include a probe that detects non-methylated DNA. It is well within the skill of the person in the art to design a probe set in accordance with the present invention and which detects two or more methylation patterns for a nucleic acid region of interest but which does not detect unmethylated DNA. Where the primers that are used are methylation specific, the issue of whether or not the probe set includes a probe directed to the non-methylated form of the nucleic acid target of interest is less significant.

According to this embodiment there is provided a method for detecting the cytosine methylation of a nucleic acid target of interest, which nucleic acid target may be characterised by a region of partial cytosine methylation, said method comprising:
  (i) contacting a nucleic acid sample with an agent which modifies unmethylated cytosine residues;
  (ii) contacting a DNA form of the sample of step (i) with:
    (a) methylation specific forward and reverse primers designed to amplify one or more fully or partially methylated forms of the modified region of partial cytosine methylation; and
    (b) one or more probes directed to said region of partial methylation wherein said one or more probes collectively hybridise to at least two differing methylation patterns at said region, and wherein said probe incorporates a detection means;
  (iii) amplifying the DNA sample of step (ii) wherein the extension of said primers along said target of interest effects the detection of said hybridised probe; and (iv) qualitatively or quantitatively analysing the detection output of step (iii).

In another embodiment, said target of interest is a DNA gene target and more preferably BCAT1, IKZF1, IRF4, GRASP, CAHM, SOX21, SLC6A15, NPY, ST8SIA1, ZSCAN18, COL4A2, DLX5, FGF5, FOXF1, FOXI2 or SDC2, preferably IKZF1.

In still another embodiment, said agent that modifies unmethylated cytosine residues is sodium bisulfite.

The size of the DNA regions to be amplified by the method of the present invention can be determined by the person of skill in the art and will depend upon factors such as the size of the region to which the probe must bind and the distribution, along the DNA target sequence, of the CpG dinucleotide clusters to which the primers are directed. To this end the amplification method of the present invention is designed such that the probe is directed to a DNA sequence region between the primers (i.e. an inter-primer sequence) and will therefore selectively hybridise to the amplicons that are produced as a result of amplification.

It should be understood that reference to the forward and reverse primers being "directed to" the target of interest should be understood to mean that the primers hybridise and amplify either all or part of the target in issue. For example, where the target of interest is a gene target, the primers may be designed to hybridise to and amplify a smaller section subregion of the gene, such as all or part of the promoter region. As would be appreciated by the person of skill in the art, it is generally desirable to generate and analyse smaller sized amplicons rather than large amplicons.

As detailed hereinbefore, the method of the present invention provides a reliable and accurate means of quantitatively (or qualitatively) screening for a methylated DNA target where partial methylation exists. This is enabled by virtue of the design and application of a probe or pool of probes that are designed to detect all potential partial methylation patterns for a given region of interest. It has been further determined that the use of a heterogeneous pool of probes of this type does hybridise effectively to, and enable detection of, the entire range of partially methylated forms of DNA which are present in the DNA sample being screened.

Accordingly, reference to "probes" should be understood as a reference to any molecule comprising a sequence of nucleotides, or functional derivatives or analogues thereof, the function of which includes the hybridisation of at least one region of said nucleotide sequence with a target nucleic acid molecule, specifically the region of potential partial methylation. The nucleic acid probe may comprise non nucleic acid components. Specifically, the nucleic acid probe also comprises a detection means, such as a fluorescent tag or some other component that facilitates the functioning of the molecule, such as the detection or immobilisation of the molecule. Reference to "detection means" should be understood as a reference to the incorporation of any means that enables detection of the probe. The detection means may facilitate either qualitative or quantitative detection, although quantitative is of particular utility. The detection means may take the form of a detectable moiety or agent, such as a fluorophore or radioisotope. Alternatively the detection means may enable the physical isolation of the probe, from the reaction mixture, for analysis, such as via magnetic beads or a biotin-streptavidin system.

Without limiting the present invention in any way, the individual probe components can be either all labelled with the same detection agent (e.g. fluorophore) or each probe component can be labelled with a different agent (e.g. different emission wavelength fluorophores). The disclosed example uses a degenerate probe mixture such that all probe components are labelled with the same fluorophore and thus any one or more of the (eight) degenerate probes that binds will give a positive signal in real-time PCR. The exact level of partial methylation across the target region is not interrogated. An alternative approach is to attach different fluorophores to each of the (eight) probes and to discriminate between bases that are methylated (or not) based on the wavelength(s) detected. This approach may be informative for cancer staging if, for instance, partial methylation was a feature of early-stage cancers and full methylation a feature of later stage cancers. Present real-time PCR instruments can detect up to six different fluorophores, but other techniques are available to interrogate multiple features in one sample (bead-based fluorescent sorting, for example). In such a case, each probe could be attached to a bead that could be sorted independently.

For example, the present invention encompasses the use of real-time quantitative forms of PCR, such as, for example, TaqMan (Holland et al., *Proc. Natl. Acad. Sci. USA*, 88, 7276-7280, 1991; Lee et al., *Nucleic Acid Res.* 21, 3761-3766, 1993) to perform this embodiment. For example, the MethyLight method of Eads et al., *Nucl. Acids Res.* 28: E32, 2000 uses a modified TaqMan hydrolysis-probe assay to detect methylation of a CpG dinucleotide. Essentially, this method comprises treating a nucleic acid sample with bisulfite and amplifying nucleic acid comprising one or more CpG dinucleotides that are methylated in a neoplastic cell and not in a control sample using an amplification reaction, e.g., PCR. The amplification reaction is performed in the presence of three oligonucleotides, a forward and reverse primer that flank the region of interest and a probe that hybridizes between the two primers to the site of the one or more methylated CpG dinucleotides. The probe is dual labelled with a 5' fluorescent reporter and a 3' quencher (or vice versa). When the probe is intact, the quencher dye absorbs the fluorescence of the reporter due to their proximity. Following annealing of to the PCR product the probe is cleaved by 5' to 3' exonuclease activity of, for example, Taq DNA polymerase. This cleavage releases the reporter from the quencher thereby resulting in an increased fluorescence signal that can be used to estimate the initial template methylation level. By using a probe or primer that selectively hybridizes to unmutated nucleic acid (i.e. methylated nucleic acid) the level of methylation is determined, e.g., using a standard curve.

Alternatively, rather than using a labelled probe that requires cleavage, a probe, such as, for example, a Molecular Beacon is used (see, for example, Mhlanga and Malmberg, *Methods* 25:463-471, 2001). Molecular beacons are single stranded nucleic acid molecules with a stem-and-loop structure. The loop structure is complementary to the region surrounding the one or more CpG dinucleotides that are methylated in a neoplastic sample and not in a control sample. The stem structure is formed by annealing two "arms" complementary to each other, which are on either side of the probe (loop). A fluorescent moiety is bound to one arm and a quenching moiety that suppresses any detectable fluorescence when the molecular beacon is not bound to a target sequence is bound to the other arm. Upon binding of the loop region to its target nucleic acid the arms are separated and fluorescence is detectable. However, even a single base mismatch significantly alters the level of fluorescence detected in a sample. Accordingly, the presence or absence of a particular base is determined by the level of fluorescence detected. Such an assay facilitates detection of one or more unmutated sites (i.e. methylated nucleotides) in a nucleic acid.

Fluorescently labelled locked nucleic acid (LNA) molecules or fluorescently labelled protein-nucleic acid (PNA) molecules are useful for the detection of nucleotide differences (e.g., as described in Simeonov and Nikiforov, *Nucleic Acids Research*, 30(17): 1-5, 2002). LNA and PNA molecules bind, with high affinity, to nucleic acid, in particular, DNA. Fluorophores (in particular, rhodomine or hexachlorofluorescein) conjugated to the LNA or PNA probe fluoresce at a significantly greater level upon hybridization of the probe to target nucleic acid. However, the level of increase of fluorescence is not enhanced to the same level when even a single nucleotide mismatch occurs. Accordingly, the degree of fluorescence detected in a sample is indicative of the presence of a mismatch between the LNA or PNA probe and the target nucleic acid, such as, in the presence of a methylated cytosine in a CpG dinucleotide. Preferably, fluorescently labelled LNA or PNA technology is used to detect at least a single base change in a nucleic acid that has been previously amplified using, for example, an amplification method known in the art and/or described herein.

As will be apparent to the skilled artisan, LNA or PNA detection technology is amenable to a high-throughput detection of one or more markers by immobilizing an LNA or PNA probe to a solid support, as described in Orum et al., *Clin. Chem.* 45: 1898-1905, 1999.

Preferably, methylation-dependent sequence differences are detected by methods based on fluorescence-based quantitative PCR (real-time quantitative PCR, Heid et al., *Genome Res.* 6:986-994, 1996; Gibson et al., *Genome Res.* 6:995-1001, 1996) (e.g., "TaqMan®", and "Lightcycler®" technologies). For the TaqMan® and Lightcycler® technologies, the sequence discrimination can occur at either or both of two steps: (1) the amplification step, or (2) the fluorescence detection step. In the case of the FRET hybridisation, probes format on the Lightcycler®, either or both of the FRET oligonucleotides can be used to distinguish the sequence difference. Most preferably the amplification process, as employed in all inventive embodiments herein, is that of fluorescence-based Real Time Quantitative PCR (Heid et al., *Genome Res.* 6:986-994, 1996) and employ a dual-labeled fluorescent oligonucleotide probe (TaqMan® PCR, using an ABI Prism 7700 Sequence Detection System, Perkin Elmer Applied Biosystems, Foster City, Calif.).

In one embodiment, the detection means is a fluorescent reporter molecule, more preferably, a hydrolysis probe. Reference to "hydrolysis probe" should be understood as a reference to a dual-labelled TaqMan® oligonucleotide. Without limiting the present invention to any one theory or mode of action, the 5' end of the oligonucleotide is labelled with a fluorescent reporter molecule while the 3' end is labelled with a quencher molecule. The sequence of the probe is specific for the region of interest in the amplified target molecule. The hydrolysis probe is designed so that the length of the sequence places the 5' fluorophore and the 3' quencher in close enough proximity so as to suppress fluorescence.

Hydrolysis probes are designed to bind a region of interest between the binding sites for the PCR amplification primers. During the extension phase of the PCR cycle Taq DNA polymerase synthesises the complementary strand downstream of the PCR primers. When the extension reaches the bound hydrolysis probe the 5'-3' exonuclease activity of the Taq DNA polymerase degrades the hydrolysis probe. Cleavage of the probe separates the fluorescent reporter molecule from the rest of the probe (and therefore the quencher) allowing the reporter molecule to fluoresce. The Taq DNA polymerase continues synthesising the rest of the nascent strand, thus hybridisation of the probe does not inhibit the PCR reaction. With subsequent PCR cycles the amount of fluorescent report released, and hence fluorescence, increases cumulatively. Examples of suitable reporter and quencher molecule are: the 5' fluorescent reporter dyes 6FAM ("FAM"; 2,7 dimethoxy-4,5-dichloro-5-carboxyfluorescein), and TET (6-carboxy-4,7,2',7'-tetrachlorofluorescein); and the 3' quencher dye TAMRA (6-carboxytetramethylrhodamine) (Livak et al., *PCR Methods Appl.* 4:357-362, 1995; Gibson et al., *Genome Res.* 6:995-1001, 1996; Heid et al., *Genome Res.* 6:986-994, 1996).

Accordingly, there is provided a method for detecting the cytosine methylation of a nucleic acid target of interest, which nucleic acid target may be characterised by a region of partial cytosine methylation, said method comprising:
(i) contacting a nucleic acid sample with a bisulfite agent, which converts unmethylated cytosine residues to uracil;
(ii) contacting a DNA form of the sample of step (i) with:
(a) methylation-specific forward and reverse primers designed to amplify one or more fully or partially methylated forms of the modified region of partial cytosine methylation; and
(b) one or more hydrolysis probes directed to said region of partial cytosine methylation wherein said one or more probes collectively hybridise to at least two differing methylation patterns at said region;
(iii) amplifying the DNA sample of step (ii) wherein the extension of said primers along said target of interest effects the detection of said hybridised probe; and
(iv) qualitatively or quantitatively analysing the detection output of step (iii).

In one embodiment, said nucleic acid is DNA.

In another embodiment, said bisulfite agent is a bisulfite salt, such as sodium bisulfate or ammonium bisulfite.

In still another embodiment, said DNA is the IKZF1 gene.

The probes of the present invention are designed such that they can hybridise, within a single reaction, to a DNA sequence that exhibits at least two different methylation patterns. For example, the probes may hybridises to the fully methylated sequence and to one or more partially methylated sequences. In another example, the probes may detect at least two different partially methylated forms of the DNA sequence. It should be understood that to the extent that the method of the present invention is directed to providing an accurate and reproducible means of detecting the methylation of a DNA target which exhibits both fully and partially methylated forms, this method of detection is designed to focus the probes to one discrete region of the DNA sequence which does, or is thought to, exhibit partially methylated forms. The person of skill in the art would understand, however, that the DNA target may also exhibit partial methylation patterns at regions of the DNA sequence other than the region targeted by the probe. It should therefore be understood that the present method is limited to detecting and assessing partial methylation at the DNA regions to which the probe is directed but not to any other regions of the DNA target. Accordingly, to the extent that one is screening a particular gene target, the method of the present invention is designed to detect all of the partially methylated forms of that gene that exhibit partial methylation at the site to which the probe is directed. However, to the extent that the subject gene may also exhibit partial methylation at other sites along its sequence, these partially methylated forms will not be detected if the probe is not directed to these methylation sites. It would also be appreciated by the skilled person, however, that to the extent that more than one region of potential partial methylation is of interest, the method can be adapted to include the use of probes directed to multiple such regions, provided that these regions are located between the amplification primer pairs.

Reference herein to the subject probe or probes hybridising to at least two "differing methylation patterns at said region" should be understood to mean that the probes that are used in the method of the invention are all designed to hybridise to the same DNA sequence region. However, this DNA sequence region, which is methylated, may exhibit either full methylation or a range of partially methylated forms, this being referred to a "differing methylation patterns" or "differential methylation". As the number of methylated CpG dinucleotides present in this region increase, the number of potentially different partially methylated patterns increases. For example, and as described earlier, in addition to the fully methylated form of IKZF1 at Chr7:50304323-50304349, there are 7 differing methylation patterns between the amplification primers including 6 partially methylated forms and the fully unmethylated form. The method of the present invention has been designed to enable the detection of all differentially methylated forms of a DNA target of interest, although depending on the circumstances of the situation, one may seek to only screen for some, but not all, the partial methylation forms of a particular DNA target. For example, if it is known that there are two predominant partially methylated forms, screening for just these two may improve diagnostic accuracy sufficiently. It is well within the skill of the person in the art to make this assessment and appropriately design a probe set.

Accordingly, in another embodiment the present invention is directed to a method for detecting the cytosine methylation of a nucleic acid target of interest, which nucleic acid target may be characterised by a region of partial cytosine methylation, said method comprising:
(i) contacting a nucleic acid sample with an agent which modifies unmethylated cytosine residues;
(ii) contacting the DNA form of the sample of step (i) with:
  (a) forward and reverse primers designed to amplify one or more fully or partially methylated forms of the modified region of partial cytosine methylation; and
  (b) one or more probes directed to said region of partial cytosine methylation wherein said one or more probes collectively hybridise to all full and partial methylation patterns at said region and wherein said probe incorporates a detection means;
(iii) amplifying the DNA sample of step (ii) wherein the extension of said primers along said target of interest effects the detection of said hybridised probe; and
(iv) qualitatively or quantitatively analysing the detection output of step (iii). In one embodiment said DNA target is a gene target, preferably BCAT1, IKZF1, IRF4, GRASP, CAHM, SOX21, SLC6A15, NPY, ST8SIA1, ZSCAN18, COL4A2, DLX5, FGF5, FOXF1, FOXI2 or SDC2, preferably IKZF1.

In another embodiment said agent is a bisulfite salt such as sodium bisulfite or ammonium bisulfite.

In still another embodiment said primers are methylation specific primers.

In yet still another embodiment said probes are hydrolysis probes.

Accordingly, there is provided a method for detecting the cytosine methylation of a gene target, which gene target may be characterised by a region of partial cytosine methylation, said method comprising:
(i) contacting a DNA sample with sodium bisulfite to convert unmethylated cytosine residues to uracil;
(ii) contacting the DNA sample of step (i) with:
  (a) methylation specific forward and reverse primers designed to amplify one or more fully or partially methylated forms of the modified gene; and
  (b) one or more hydrolysis probes directed to said region of partial cytosine methylation wherein said one or more probes collectively hybridise to at least two differing methylation patterns at said region;
(iii) amplifying the DNA sample of step (ii) wherein the extension of said primers along said DNA target of interest effects the detection of said hybridised probe; and
(iv) qualitatively or quantitatively analysing the detection output of step (iii).

In yet another embodiment, said gene is IKZF1 and said primers comprise the sequences:

```
(FORWARD PRIMER):
                                        SEQ ID NO: 3
Chr7: 50304271 GACGACGTAT TTTTTTCGTG

TTTC 50304294

(REVERSE PRIMER):
                                        SEQ ID NO: 4
Chr7: 50304365 GCGCACCTCT CGACCG 50304350
``` or substantially similar sequences and said probes comprise the sequences:

```
SEQ ID NO: 5:
Chr7: 50304323 TTTGTATCGG AGTAGCGATT

CGGGAGG 50304349

SEQ ID NO: 6:
Chr7: 50304323 TTTGTATCGG AGTAGCGATT

TGGGAGG 50304349

SEQ ID NO: 7:
Chr7: 50304323 TTTGTATCGG AGTAGTGATT

CGGGAGG 50304349

SEQ ID NO: 8:
Chr7: 50304323 TTTGTATTGG AGTAGCGATT

CGGGAGG 50304349

SEQ ID NO: 9:
Chr7: 50304323 TTTGTATCGG AGTAGTGATT

TGGGAGG 50304349

SEQ ID NO: 10:
Chr7: 50304323 TTTGTATTGG AGTAGCGATT

TGGGAGG 50304349

SEQ ID NO: 11:
Chr7: 50304323 TTTGTATTGG AGTAGTGATT

CGGGAGG 50304349

SEQ ID NO: 12:
Chr7: 50304323 TTTGTATTGG AGTAGTGATT

TGGGAGG 50304349
``` or substantially similar sequences.

In yet another embodiment, said primers comprise the sequences SEQ ID NO:3 and SEQ ID NO:4 or substantially similar sequences and said probe comprises the sequence SEQ ID NO:19 or substantially similar sequence.

In still another embodiment, said primers comprise the sequences SEQ ID NO:3 and SEQ ID NO:4 or substantially similar sequences and said probe comprises the sequence SEQ ID NO:20 or substantially similar sequence.

In yet still another embodiment, said methylation specific amplification assay is directed to the bisulfite converted DNA strand that is the complement of SEQ ID NO:1 and said probes comprise the sequence SEQ ID NO:21 or SEQ ID NO:22 or substantially similar sequences.

In still another embodiment, said primers comprise the sequences SEQ ID NO:3 and SEQ ID NO:4 or substantially similar sequences and the probe set comprises one or more of SEQ ID NO:23-30 or substantially similar sequences.

In a further embodiment, said methylation specific amplification assay is directed to the bisulfite converted DNA strand that is the complement of SEQ ID NO:1, said primer set includes primers comprising the sequences SEQ ID NO:47 and SEQ ID NO:48 and said probe set comprises the sequences SEQ ID NO:31-38 and/or SEQ ID NO:39-46.

In yet another embodiment, said probes collectively hybridise to all full and partial methylation patterns at said region. In yet another further embodiment, said primer set includes primers which comprise one or more of the SEQ ID NO:49-62 and SEQ ID NO:63-76 sequences or substantially similar sequences.

In still yet another embodiment, said primer set includes primers which comprise one or more of SEQ ID NO:77 and SEQ ID NO:78 sequences or substantially similar sequences.

It should be understood that the subject primers may correspond to the sequences disclosed above or may be substantially similar. Alternatively, these sequences or a substantially similar sequence may represent a subregion within a larger primer molecule. Reference to a "substantially similar sequence" should be understood as a reference to a sequence which may exhibit some minor difference in sequence but which nevertheless functions to amplify the same DNA target as the sequence to which it is substantially similar.

Without limiting the present invention to any one theory or mode of action, it has been determined that in the context of the following DNA regions of IKZF1:

(IKZF1 diagnostic region-wild type DNA):
                                            SEQ ID NO: 1
Chr7: 50304271 GA<u>CG</u>A<u>CG</u>CAC CCTCTC<u>CG</u>TG TCC<u>CG</u>CTCTG <u>CG</u>CCCTTCTG <u>CGCG</u>CCCCGC TCCCTGTAC<u>C</u> <u>G</u>GAGCAGC<u>GA</u>

TC<u>CG</u>GGAGG<u>C</u> <u>G</u>GC<u>CG</u>AGAGG TG<u>CGC</u> 50304365 the following cytosines are methylated with high frequency in colon derived neoplastic DNA (Chr 7, GRCh38/Hg38 co-ordinates): 50304273, 50304276, 50304287, 50304294, 50304301, 50304311, 50304313, 50304318, 50304330, 50304338, 50304343, 50304350, 50304354, 50304363, 50304365. This embodiment of the present invention is directed to screening for partial methylation on cytosine residues 50304330, 50304338 and 50304343. Detecting any combination of methylation across these three CpG sites in the IKZF1 locus in recovered bisulfite converted DNA isolated from plasma can be used to increase the diagnostic sensitivity for colorectal cancer. In accordance with this embodiment, treatment of DNA with sodium-bisulphite converts cytosines to uracil, but leaves 5'methylcytosine residues unaffected. PCR oligonucleotide primers are designed (SEQ ID NOs 3 and 4) that specifically prime to SEQ ID NO:2 of which disease-specific methylation is required of all cytosine residues 50304273, 50304276, 50304287, 50304294, 50304350, 50304354, 50304363 and 50304365. Methylation of any (or none) of three cytosine residues 50304330, 50304338 and 50304343 is detected using the degenerate hydrolysis probe mixture (SEQ ID NOs 5-12) (for example, a TaqMan degenerate probe mixture).

The probes of the present invention "collectively" bind to the range of partially and fully methylated sequences that are sought to be detected. By "collectively" is meant that the cohort of probes that is selected for use are able, either individually or by virtue of the promiscuity of hybridisation of an individual probe, to bind to the range of partially methylated forms of the DNA target that are sought to be detected. Without limiting the present invention to any one theory or mode of action, the sequence of the DNA region that is to be interrogated by the probe will be known to the skilled person, as will the position of the methylated CpG dinucleotides. Based on this sequence information, and as exemplified earlier in relation to IKZF1, the full range of possible full and partial methylation patterns can be predicted. Probes can then be designed that either each individually bind to a unique methylation pattern or that exhibit promiscuity and can bind to more than one methylation pattern. As has been determined a probe directed to a fully methylated sequence does not bind to a partially methylated sequence, even where the difference between the fully methylated sequence and the partially methylated sequence is as little as the lack of methylation of one cytosine residue. It has also been determined, however, that if either a heterogenous pool of methylation specific probes or probes which are designed to bind promiscuously across both methylated and non-methylated cytosines are used in an amplification assay, an accurate result can be obtained in relation to the methylation of the target of interest.

The probes that are designed to hybridise to one specific fully or partially methylated sequence pattern can be generated by methods which are well known to those of skill in the art. In relation to the probes that exhibit promiscuity, in that they can bind to more than one methylation pattern, this design can also be achieved by several methods which are known to those of skill in the art. For example, one or more base positions in the probe (such as in a 5'-hydrolysis probe) are not unique, but are a mixture of two bases, namely cytosine or thymidine. If only one CpG site is interrogated for methylation (or not) then such degenerate oligonucleotide would be a mixture of two different oligonucleotide sequences, e.g. --atCGat-- and --atTGat--. If two CpG sites were interrogated, then the degenerate oligonucleotide cocktail would be a mixture of four different sequences. The IKZF1 example provided herein is an example where partial methylation of three CpG sites are interrogated by using a degenerate 5'-hydrolysis oligonucleotide probe mixture consisting of eight different oligonucleotide sequences (SEQ ID NOs 5-12). The mixture can detect all possible combinations of methylation within the three CpG sites residing in Chr7 coordinates 50304330, 50304338 and 50304343. This example improves the diagnostic sensitivity of the IKZF1 methylation assay.

As detailed earlier, the probes can be any variance of detection probes such as TaqMan, Scorpions, Beacons, etc. The probe mixture may be synthesised (in the context of the IKZF1 example) as
(i) 8-fold redundant in one synthesis (by blending C and T during synthesis);

(ii) three different two-fold redundant probes and mixed;
(iii) one two-fold and one four-fold redundant probes and mixed; or
(iv) eight different unique probes and mixed.

The probe could also be a single sequence with either an abasic spacer (e.g. 5-nitro-indole or 3-nitro-pyrrole) at each interrogated C/T base, or with an Inosine at each interrogated C/T base. A single sequence "promiscuous" probe containing one or more abasic spacer(s) would have only one annealing temperature, but the melting temperature of the abasic spacer(s) containing probe would be significantly lower than the probe detecting methylation on all interrogated CpG sites. Thus a promiscuous probe with abasic spacer(s) would need to be significantly longer than the probe targeting methylated CpG sites only. Inosine will allow base-pairing with any base, but has a preference in the order C>A>G>T. As this sequence is in the opposite strand to the probe, the probe would be annealing to A (=T, unmethylated) or G (=C, methylated) in this case. Both these options are less specific than the promiscuous probe. Because they allow pairing to one of 4 bases at 3 positions, they are in fact 64-fold degenerate (vs 8-fold), and thus rely more heavily on the methylation specificity of the primers. Abasic-spacer or Inosine-containing probes have the benefit of being a single oligonucleotide component, rather than a mixture of 8 oligonucleotide components.

The probe could also have a pyrimidine (C or T) analogue at each potential partially methylated C position. For example, the analogue, 6H,8H-3,4-dihydropyrimido[4,5-c][1,2]oxazin-7-one, is a single "base" that will base pair with both G and A (which are the two options in the opposite strand). From one study it has a 60% preference for A (=T=unmethylated) and 40% for G (=C=methylated). (Hill et al., *Proc Natl Acad Sci USA.,* 95:4258-4263, 1998). The benefit here is that this probe is a single oligonucleotide that will bind all 8 possible methylation combinations with approximately equal affinity. It would be appreciated that since some of the individual probe sequences will contain thymidine instead of cytosine bases, which lowers the annealing temperature, some of the probe sequence(s) may need to be extended in length to compensate for the lower annealing temperature. An alternate approach would be to include chemical modifications that increase annealing temperature (such as major groove binding bases). It should also be understood that the proportions of each base at the degenerate position(s) of the probe do not necessarily have to be 50/50. For example if one identified that a specific C residue was methylated in 80% of true cancer cases but not methylated in 20% of true cancer cases, one could make a probe with 80% C and 20% T at this position to match the incidence of methylation.

As would be appreciated by those skilled in the art, and as detailed hereinbefore the probe sequence(s) can be designed to hybridise to the opposite strand as well. These probe sequence designs on the opposite strand would have a G or an A at the degenerate position (or Inosine or abasic spacer as above) to interrogate partial methylation. The pyrimidine analogue mentioned above would now change to a purine analogue, N6-methoxy-2,6-diaminopurine, that will bind both T and C.

The probes and/or primers of the present invention are also assessed to determine that they do not self-prime or form primer dimers (e.g. with another probe or primer used in a detection assay). Furthermore, a probe or primer (or the sequence thereof) is often assessed to determine the temperature at which it denatures from a target nucleic acid (i.e. the melting temperature of the probe or primer, or Tm). Methods for estimating Tm are known in the art and described, for example, in Santa Lucia, *Proc. Natl. Acad. Sci. USA,* 95: 1460-1465, 1995 or Breslauer et al., *Proc. Natl. Acad. Sci. USA,* 83: 3746-3750, 1986.

Methods for producing/synthesizing a probe or primer of the present invention are known in the art. For example, oligonucleotide synthesis is described, in Gait (Ed) (In: Oligonucleotide Synthesis: A Practical Approach, IRL Press, Oxford, 1984). For example, a probe or primer may be obtained by biological synthesis (e.g. by digestion of a nucleic acid with a restriction endonuclease) or by chemical synthesis. For short sequences (up to about 100 nucleotides) chemical synthesis is preferable.

For longer sequences standard replication methods employed in molecular biology are useful, such as, for example, the use of M13 for single stranded DNA as described by Messing, *Methods Enzymol,* 101, 20-78, 1983. Other methods for oligonucleotide synthesis include, for example, phosphotriester and phosphodiester methods (Narang, et al. *Meth. Enzymol* 68: 90, 1979) and synthesis on a support (Beaucage, et al. *Tetrahedron Letters* 22: 1859-1862, 1981) as well as phosphoramidate technique, Caruthers, M. H., et al., "Methods in Enzymology," Vol. 154, pp. 287-314 (1988), and others described in "Synthesis and Applications of DNA and RNA," S. A. Narang, editor, Academic Press, New York, 1987, and the references cited therein. Probes comprising locked nucleic acid (LNA) are synthesized as described, for example, in Nielsen et al., *J. Chem. Soc. Perkin Trans.,* 1:3423, 1997; Singh and Wengel, *Chem. Commun.* 1247, 1998. While, probes comprising peptide-nucleic acid (PNA) are synthesized as described, for example, in Egholm et al., *Am. Chem. Soc.,* 114: 1895, 1992; Egholm et al., *Nature,* 365: 566, 1993; and Orum et al., *Nucl. Acids Res.,* 21: 5332, 1993.

The DNA or RNA sample of the present invention is amplified using primers that flank the region of methylation of interest. As detailed hereinbefore, this "region" may be selected to encompass a small or a substantial part of the length of the gene. In the latter case the amplicons that are generated would be quite long. However, in a particular embodiment, the region may correspond to a much shorter stretch of the gene where one or more CpG dinucleotides are clustered. In this case the amplicons that are generated would be significantly shorter.

Facilitating the interaction of the primers and probes with the target DNA may be performed by any suitable method. Those methods will be known to those skilled in the art. To this end, it should be understood that the primers and probes can be incorporated into the reaction tube at any suitable time point. While incorporation is generally prior to the commencement of the initial amplification cycles, incorporation of one or more additional primers may be performed subsequently to the initial amplification cycles. The mode of incorporation of the primers will depend on how the skilled person is seeking to perform the amplification reaction but, in general, for ease of use and avoidance of contamination, it is usually desirable to be able to perform the entire reaction in a single tube. Nevertheless, any other method of achieving the steps of the invention can be used. Accordingly, reference to "contacting" the sample with the primer or antisense oligonucleotide should be understood as a reference to facilitating the mixing of the primer with the sample such that interaction (for example, hybridisation) can occur. Means of achieving this objective would be well known to those of skill in the art.

As detailed hereinbefore, where multiple methylated DNA regions are to be amplified, the skilled person may design multiplexed amplification reactions. Alternatively, several individual amplification reactions that each use one unique primer pair may be performed. These methods become relevant where one is amplifying two or more separate methylation regions or where the methylation of more than one gene is to be analysed. In this case, one may divide the sample into two aliquots, for example, after the sodium bisulfite conversion, if two genes are sought to be analysed (such as BCAT1 and IKZF1), with each aliquot then being amplified using the one or more sets of forward and reverse primers directed to the relevant methylation sequence regions of that gene. Alternatively, a multiplexed reaction can be performed on a single sample wherein the reaction is multiplexed in terms of the use of a primer pair and hydrolysis probe set directed to a selected methylation sequence region of one gene and the use of another set of primers and a hydrolysis probe set directed to a selected methylation sequence region of another gene. As would be familiar to the skilled person, multiplexed reactions can be designed to be performed with two, three or more sets of primers and hydrolysis probes in the context of two or more methylation sequence regions and/or two or more genes. It should be understood that it would be well within the skill of the person in the art to appropriately design multiplexed or nested amplification reactions.

The amplification step of the present invention leads to extension of the hybridised primers along the DNA target of interest. As detailed hereinbefore it is the generation of the primer extension molecule that effects the detection of the hybridised dual-labelled hydrolysis probe. The means by which this can be effected would be well known to the skilled person as would the fact that the detection means output, which is generated upon amplicon production, can be analysed either qualitatively or quantitatively, the latter being a particularly preferred means. To this end, it should be understood that the detection of the probe is only effected when the primers extend along the DNA sequence to which the probe is hybridised and displace, cleave or otherwise effect a modification to the probe which enables its detection means to become functional (e.g. activated or revealed) and thereby detectable by either qualitative or quantitative means.

Although the preferred application of this method is to assess methylation levels for the purpose of diagnosing disease onset (such as neoplasia development or predisposition thereto), the detection of converse changes in the levels of said methylation may be desired under certain circumstances, for example, to monitor the effectiveness of therapeutic or prophylactic treatment directed to modulating a neoplastic condition, such as adenoma or adenocarcinoma development. For example, where elevated levels of methylation indicate that an individual has developed a condition characterised by adenoma or adenocarcinoma development, screening for a decrease in the levels of methylation subsequently to the onset of a therapeutic treatment regime may be utilised to indicate successful clearance of the neoplastic cells. In another example, one can use this method to test the tissue at the margins of a tumour resection in order to determine whether the full margin of the tumour has been removed.

The present method can therefore be used in the diagnosis, prognosis, classification, prediction of disease risk, detection of recurrence of disease, selection of treatment of a number of types of neoplasms and monitoring of neoplasms. A cancer at any stage of progression can be detected, such as primary, metastatic, and recurrent cancers. Still further, this method has applications in any other context where analysis of DNA and RNA methylation is necessitated.

Using neoplasm development as a non-limiting example, the present invention provides methods for determining whether a mammal (e.g., a human) has neoplasia, whether a biological sample taken from a mammal contains neoplastic cells or DNA derived from neoplastic cells, estimating the risk or likelihood of a mammal developing a neoplasm, monitoring the efficacy of anti-cancer treatment, or selecting the appropriate anti-cancer treatment in a mammal with cancer. Such methods are based on the determination that many neoplastic cells have a different methylation status than normal cells. Accordingly, by determining whether or not a cell contains differentially methylated sequences it is possible to determine that a cell is neoplastic.

The method of the invention can be used to evaluate individuals known or suspected to have neoplasia, or as a routine clinical test, i.e., in an individual not necessarily suspected to have a neoplasia. Further diagnostic assays can be performed to confirm the status of neoplasia in the individual.

Further, the present methods may be used to assess the efficacy of a course of treatment. For example, the efficacy of an anti-cancer treatment can be assessed by monitoring DNA methylation over time in a mammal having cancer. For example, a reduction or absence of methylation in any of the relevant diagnostic sequences in a biological sample taken from a mammal following a treatment, compared to a level in a sample taken from the mammal before, or earlier in, the treatment, indicates efficacious treatment.

The method of the present invention is therefore useful as a one-time test or as an on-going monitor of those individuals thought to be at risk of disease development or as a monitor of the effectiveness of therapeutic or prophylactic treatment regimes. In these situations, mapping the modulation of methylation levels in any one or more classes of biological samples is a valuable indicator of the status of an individual or the effectiveness of a therapeutic or prophylactic regime that is currently in use. Accordingly, the method of the present invention should be understood to extend to monitoring for increases or decreases in methylation levels in an individual relative to their normal level, or relative to one or more earlier methylation levels determined from a biological sample of said individual.

In a related aspect, in addition to developing a method for accurately detecting both full and partial methylation, the present inventors have unexpectedly determined that in the context of diagnostic protocols, and contrary to accepted dogma, screening for all forms of methylation is a patient or other sample can in fact provide a more sensitive result than if only full methylation is screened for. Previous concerns that screening for partial methylation would actually obscure the diagnostic results has been shown to not create any problems when the method of the present invention is used. In fact, the sensitivity of the diagnostic result is improved.

Accordingly, in another aspect the present invention is directed to a method for diagnosing or monitoring a condition in a patient which condition is characterised by modulation of the cytosine methylation of a nucleic acid target of interest and which target is characterised by a region of partial methylation, said method comprising:
 (i) contacting a nucleic acid sample from said patient with an agent which modifies unmethylated cytosine residues;
 (ii) contacting the DNA form of the nucleic acid sample of step (i) with:
  (a) forward and reverse primers designed to amplify one or more fully or partially methylated forms of the modified gene; and
  (b) one or more probes directed to said region of partial cytosine methylation wherein said one or more probes collectively hybridise to at least two differing methylation patterns at said region and wherein said probe incorporates a detection means;
 (iii) amplifying the DNA sample of step (ii) wherein the extension of said primers along said target of interest effects the detection of said hybridised probe; and
 (iv) qualitatively or quantitatively analysing the detection output of step (iii).

In one embodiment, said target is DNA or RNA, preferably the promoter region.

In another embodiment said condition is a neoplastic condition.

In another embodiment said DNA or RNA target is a gene such as BCAT1, IKZF1, CAHM, GRASP, IRF4, SOX21, SLC6A15, NPY, ST8SIA1, ZSCAN18, COL4A2, DLX5, FGF5, FOXF1, FOXI2 or SDC2.

In still another embodiment said agent is a bisulfite salt, such as sodium bisulfite or ammonium bisulfite.

In yet still another embodiment said probes are hydrolysis probes.

In a further aspect there is provided a diagnostic kit for detecting the cytosine methylation of a region of a nucleic acid target of interest, said kit comprising:
 (i) forward and reverse primers designed to amplify one or more fully or partially methylated forms of a DNA form of said nucleic acid region of partial cytosine methylation in which unmethylated cytosine residues have been modified;
 (ii) one or more probes directed to said region of partial cytosine methylation which probes are capable of collectively hybridising to at least two differing methylation patterns.

In one embodiment, said primers are methylation specific primers.

In another embodiment said probes are hydrolysis probes.

In still another embodiment said agent is an agent which modifies unmethylated cytosine residues.

In yet another embodiment said agent is a bisulphite salt, such as sodium bisulphite or ammonium bisulphite.

In a further embodiment, said kit additionally comprises reagents to effect DNA amplification and/or detection.

To the extent that said gene of interest is IKZF1, said primers and probes are directed to detecting methylation at one or more of the Chr7:50304323050304349, Chr7:50303300-50304923 or Chr7:50399869-50400702 regions of the IKZF1 gene.

In a further embodiment, the primer set includes primers which comprise one or more of:
 (i) the SEQ ID NO:3 and SEQ ID NO:4 sequences or substantially similar sequences;
 (ii) the SEQ ID NO:49-62 and SEQ ID NO:63-76 sequences or substantially similar sequences; or
 (iii) the SEQ ID NO:77 and SEQ ID NO:78 sequences or substantially similar sequences.

In another further embodiment, the probe set includes probes comprising one or more of:
 (i) the SEQ ID NO:5-12 sequences or substantially similar sequences;
 (ii) the SEQ ID NO:19 sequence or substantially similar sequence;
 (iii) the SEQ ID NO:20 sequence or substantially similar sequence; or
 (iv) the SEQ ID NO:23-30 sequences or substantially similar sequences.

In still another embodiment where said kit is directed to amplifying the bisulfite converted DNA strand that is the complement of the SEQ ID NO:1 region, said primer set includes primers which comprise one or both of the SEQ ID NO:47 and SEQ ID NO:48 sequences or substantially similar sequences.

In yet another embodiment, where said kit is directed to amplifying the bisulfite converted DNA strand that is the complement of the SEQ ID NO:1 region, said probe set includes probes which comprise one or more of:
  (i) the SEQ ID NO:21 sequence or substantially similar sequence;
  (ii) the SEQ ID NO:22 sequence or substantially similar sequence;
  (iii) the SEQ ID NO:31-38 sequences or substantially similar sequences; and/or the SEQ ID NO:39-46 sequences or substantially similar sequences.

The present invention is further described by reference to the following non-limiting examples.

Example 1

Identification of Partially Methylated IKZF1 DNA in Circulation of Colorectal Cancer Patients Plasma was drawn from 2,109 colonoscopy-examined subjects including 134 cancer cases. Cell-free DNA was extracted using the QS CNA 4 mL plasma kit (Qiagen) as recommended by manufacturer on a QIASymphony. The resulting DNA was bisulphite-converted and purified using the EpiTect Fast and EpiTect Plus kits on QIACubes as recommended by manufacturer (Qiagen). The recovered bisulphite converted DNA was analysed as triplicate input in a multiplexed real-time PCR assay using the mastermix QuantiTect NoROX as recommended by manufacturer including oligonucleotides SEQ ID NO:3, SEQ ID NO:4 and SEQ ID NO:5 in addition to BCAT1 bisulphite-conversion and methylation specific oligos (SEQ ID NOs 13, 14 and 15, targeting the 102 nt amplicon residing on chr12: 24949058-24949159) and bisulphite conversion specific oligonucleotides SEQ ID NOs16, 17, 18, which targeted the control DNA gene, ACTB, on chromosome 7.

The detection of methylated BCAT1 and IKZF1 was performed in a total PCR reaction of 30 μL using the following LC480 II cycling conditions: 1×[95° C., 15 min], 50×[95° C., 15 sec; 62° C., 40 sec (with acquisition, FAM, HEX, TexRed)], 1×[40° C., 10 sec, and hold].

```
SEQ ID NO: 1 (IKZF1 diagnostic region - wild type DNA):
Chr7: 50304271 GACGACGCAC CCTCTCCGTG TCCCGCTCTG CGCCCTTCTG CGCGCCCCGC TCCCTGTACC

GGAGCAGCGA TCCGGGAGGC GGCCGAGAGG TGCGC 50304365

SEQ ID NO: 2 (Bisulphite converted, fully methylated version of SEQ ID NO: 1 after PCR
amplification):

Chr7: 50304271   GACGACGTAT TTTTTTCGTG TTTCGTTTTG CGTTTTTTTG CGCGTTTCGC TTTTTGTATC

GGAGTAGCGA TTCGGGAGGC GGTCGAGAGG TGCGC(G) 50304365

SEQ ID NO: 3     Chr7: 50304271   GACGACGTAT TTTTTTCGTG TTTC            50304294   (IKZF1 FWD)

SEQ ID NO: 4     Chr7: 50304365   GCGCACCTCT CGACCG                    50304350   (IKZF1 REV)

SEQ ID NO: 5     Chr7: 50304323   TTTGTATCGG AGTAGCGATT CGGGAGG        50304349   (IKZF1 Probe A)

SEQ ID NO: 6     Chr7: 50304323   TTTGTATCGG AGTAGCGATT TGGGAGG        50304349   (IKZF1 Probe B)

SEQ ID NO: 7     Chr7: 50304323   TTTGTATCGG AGTAGTGATT CGGGAGG        50304349   (IKZF1 Probe C)

SEQ ID NO: 8     Chr7: 50304323   TTTGTATTGG AGTAGCGATT CGGGAGG        50304349   (IKZF1 Probe D)

SEQ ID NO: 9     Chr7: 50304323   TTTGTATCGG AGTAGTGATT TGGGAGG        50304349   (IKZF1 Probe E)

SEQ ID NO: 10    Chr7: 50304323   TTTGTATTGG AGTAGCGATT TGGGAGG        50304349   (IKZF1 Probe F)

SEQ ID NO: 11    Chr7: 50304323   TTTGTATTGG AGTAGTGATT CGGGAGG        50304349   (IKZF1 Probe G)

SEQ ID NO: 12    Chr7: 50304323   TTTGTATTGG AGTAGTGATT TGGGAGG        50304349   (IKZF1 Probe H)

SEQ ID NO: 13:   Chr12: 24949058  GTTTTTTTGT TGATGTAATT CGTTAGGTC      24949086   (BCAT1 FWD)

SEQ ID NO: 14:   Chr12: 24949159  CAATACCCGA AACGACGACG                24949140   (BCAT1 REV)

SEQ ID NO: 15:   Chr12: 24949094  TTCGTCGCGA GAGGGTCGGTT               24949114   (BCAT1 Probe)

SEQ ID NO: 16:   Chr7: 5532633    GGAGTTTTTG TTTTTTGGTT AGTTG          5532609    (ACTB FWD)

SEQ ID NO: 17:   Chr7: 5532545    CAAAATAAAA TACAAAACAA ACCTAATCC      5532573    (ACTB REV)

SEQ ID NO: 18:   Chr7: 5532607    ATGGAGGTTT AGTGGTAATA TAGGTTTTGT TTGG 5532574   (ACTB probe)
```

Of the 134 cancers, 74 and 62 were positive for BCAT1 and IKZF1 methylation, respectively. PCR products from PCR reactions that were BCAT1 methylation positive but IKZF1 methylation negative were diluted and reamplified using a SYBR-green IKZF1 assay that included SEQ ID NO:3 and SEQ ID NO:4 primers only. The generated PCR products were run on agarose gels to reveal whether a PCR product of ~100 bp had been produced, which would confirm the existence of methylated IKZF1 DNA which however, would not have been detected originally due to the multiplex PCR assay requiring a fully methylated IKZF1 target including in the three CpG sites under the 'fully methylated' IKZF1 probe (SEQ ID NO:5). The agarose separated PCR products generated in Example 1 were purified and sequenced, which revealed evidence of partial methylation in several PCR products, including two cases of no methylation of CpG residues 50304330, 50304338 and 50304343, which would explain why the 'fully-methylated'-requiring IKZF1 probe (SEQ ID NO:5) resulted in false-negative IKZF1 results in otherwise colonoscopy-confirmed cancers. Partial methylation was also observed at other CpG sites in the IKZF1 amplicon, FIG. 1.

Conclusion

Clear evidence of partial methylation in the IKZF1 hydrolysis probe region was obtained for three of the amplicons sequenced. Two of these were colonoscopy-confirmed cancers, and were negative in the original IKZF1 real-time PCR assay with a probe designed to detect fully-methylated IKZF1 DNA.

Example 2

Detection of Partial Methylated IKZF1 in Colorectal Cancer Patients

Subsequently to the detection of partially methylated CpG sites embedded in the targeted IKZF1 amplicon sequence (SEQ ID NO:2), we generated a 'degenerate' IKZF1 5'-hydrolysis probe mixture consisting of eight different oligonucleotide sequences (SEQ ID NOs 5-12) with either a cytosine or thymidine base at each of three residue positions corresponding to the genomic coordinates Chr7: 50304330, Chr7: 50304338 and Chr7: 50304343. The oligonucleotide mixture was obtained during oligonucleotide probe production by incorporating an equal mixture of the two bases at each position.

DNA was extracted from additional 4 mL plasma from a sub-cohort (n=308) of the 2,109 patients described in Example 1. The recovered bisulphite DNA was analysed as triplicate input in a multiplexed real-time PCR assay using the mastermix QuantiTect NoROX as recommended by manufacturer including oligonucleotides SEQ ID NOs 3-18. The detection of methylated BCAT1 and fully methylated/partially methylated IKZF1 was performed in a total PCR reaction of 30 μL using the following LC480 II cycling conditions: 1×[95° C., 15 min], 50×[95° C., 15 sec; 62° C., 40 sec (with acquisition, FAM, HEX, TexRed)], 1×[40° C., 10 sec, and hold]. The PCR results were compared to the previous dataset using a multiplex PCR targeting fully methylated BCAT1 and IKZF1 amplicons only.

TABLE 1

| Phenotype | n | IKZF1 qPCR requiring fully methylated amplicon | | IKZF1 qPCR able to detect partially methylated amplicon | | BCAT1 Real-time PCR requiring fully methylated amplicon | |
|---|---|---|---|---|---|---|---|
| | | +ve | % | +ve | % | +ve | % |
| Normal | 196 | 2 | 1 | 9 | 4.6 | 15 | 8 |
| Adenoma | 84 | 1 | 0 | 5 | 6.0 | 5 | 6 |
| Cancer | 28 | 10 | 35.7 | 15 | 53.6 | 16 | 57.1 |

Conclusion:

When the 8-fold degenerate probe was tested on clinical patient samples, it gave a similar positivity rate to BCAT1 in colonoscopy-confirmed cancer samples, indicating that the problem of patient false negative calling due to partial methylation had been overcome, Table 1.

Example 3

Alternative 5'-Hydrolysis Probes

"Degenerate" Probes with Modified Bases/Base Analogues

The eight probes used in Example 2 above could be replaced by a single "promiscuous" oligonucleotide that was designed to detect all 8 variably-methylated IKZF1 probe target regions. SEQ ID NO:19 would be used with SEQ ID NO:3 and SEQ ID NO:4 as primers, and replace SEQ ID NOs 5-12. SEQ ID NO:19 would anneal to the complementary strand of the variably methylated versions of SEQ ID NO:2. SEQ ID NO:20 could also be used in place of SEQ ID NOs 5-12 and would bind to the variably methylated versions of the strand shown as SEQ ID NO:2. Those skilled in the art would also realise that a methylation-specific PCR assay could be designed from the bisulfite-converted DNA strand that is the complement of that shown as SEQ ID NO:1. Such an assay would require different "promiscuous" oligonucleotide probes, and these two options are shown as SEQ ID NO:21 and SEQ ID NO:22.

```
SEQ ID NO: 19:
Chr7: 50304323 TTTGTATZGG AGTAGZGATT

ZGGGAGG 50304349

SEQ ID NO: 20:
Chr7: 50304348 CTCCCXAATC XCTACTCCXA

TACAAAAAG 50304320

SEQ ID NO: 21:
Chr7: 50304349 TTTTTZGGAT ZGTTGTTTZG

GTATAGGG 50304322

SEQ ID NO: 22:
Chr7: 50304322 CCCTATACCX AAACAACXAT

CCXAAAAA 50304349
```

Where Z is either inosine; an abasic spacer; or 6H,8H-3,4-dihydropyrimido[4,5-c][1,2]oxazin-7-one (or a functional analogue thereof), and where X is either Inosine; an abasic spacer; or N6-methoxy-2,6-diaminopurine (or a functional analogue thereof).

Alternative 'Degenerate' 5'-Hydrolysis Probes for Detection of the Sense Strand of SEQ ID 2

The IKZF1 probes used in Example 1 (SEQ ID NO:5) or Example 2 (SEQ ID NOs 5-12) are designed to anneal to the complementary strand of SEQ ID NO:2. Those skilled in the art would also realise that analogous probes could be designed that would bind to SEQ ID NO:2. These probes would be used in a methylation-specific PCR assay with SEQ ID NO:3 and SEQ ID NO:4 and are listed below as SEQ ID NOs 23-30

```
SEQ ID NO: 23:
Chr7: 50304348 CTCCCGAATC GCTACTCCGA

TACAAAAAG 50304320

SEQ ID NO: 24:
Chr7: 50304348 CTCCCAAATC GCTACTCCGA

TACAAAAAG 50304320

SEQ ID NO: 25:
Chr7: 50304348 CTCCCGAATC ACTACTCCGA

TACAAAAAG 50304320

SEQ ID NO: 26:
Chr7: 50304348 CTCCCGAATC GCTACTCCAA

TACAAAAAG 50304320

SEQ ID NO: 27:
Chr7: 50304348 CTCCCAAATC ACTACTCCGA

TACAAAAAG 50304320

SEQ ID NO: 28:
Chr7: 50304348 CTCCCAAATC GCTACTCCAA

TACAAAAAG 50304320

SEQ ID NO: 29:
Chr7: 50304348 CTCCCGAATC ACTACTCCAA

TACAAAAAG 50304320

SEQ ID NO: 30:
Chr7: 50304348 CTCCCAAATC ACTACTCCAA

TACAAAAAG 50304320
```

'Degenerate' 5'-Hydrolysis Probes for Detection of the Bisulphite Converted Version of the Complementary Strand of SEQ ID NO:1

The methylation-specific PCR assays used in Example 1 and Example 2 are designed against the bisulfite-converted DNA strand corresponding to SEQ ID NO:1. Those skilled in the art would also realise that a methylation-specific PCR assay could be designed from the bisulfite-converted DNA strand that is the complement of that shown as SEQ ID NO:1. This would not be the complement of SEQ ID NO:2. Such an assay designed from the bisulfite-converted DNA strand that is the complement of that shown as SEQ ID NO:1 would require different probes to detect all 8 possible variably methylated forms of IKZF1. These could be single "promiscuous" oligonucleotide probes as shown in SEQ ID NOs 20 and 21 above, or could be the two sets of 8 probes shown as SEQ ID NOs 31-38, and SEQ ID NOs 39-46 below, depending on which strand of amplified DNA was being detected. Such an assay would also require additional methylation-specific PCR primers, which are shown as SEQ ID NOs:47 and 48.

```
SEQ ID NO: 31:
Chr7: 50304349 TTTTTCGGAT CGTTGTTTCG

GTATAGGG 50304322

SEQ ID NO: 32:
Chr7: 50304349 TTTTTCGGAT CGTTGTTTTG

GTATAGGG 50304322

SEQ ID NO: 33:
Chr7: 50304349 TTTTTCGGAT TGTTGTTTCG

GTATAGGG 50304322

SEQ ID NO: 34:
Chr7: 50304349 TTTTTTGGAT CGTTGTTTCG

GTATAGGG 50304322

SEQ ID NO: 35:
Chr7: 50304349 TTTTTCGGAT TGTTGTTTTG

GTATAGGG 50304322

SEQ ID NO: 36:
Chr7: 50304349 TTTTTTGGAT CGTTGTTTTG

GTATAGGG 50304322

SEQ ID NO: 37:
Chr7: 50304349 TTTTTTGGAT TGTTGTTTCG

GTATAGGG 50304322

SEQ ID NO: 38:
Chr7: 50304349 TTTTTTGGAT TGTTGTTTTG

GTATAGGG 50304322

SEQ ID NO: 39:
Chr7: 50304322 CCCTATACCG AAACAACGAT

CCGAAAAA 50304349

SEQ ID NO: 40:
Chr7: 50304322 CCCTATACCA AAACAACGAT

CCGAAAAA 50304349

SEQ ID NO: 41:
Chr7: 50304322 CCCTATACCG AAACAACAAT

CCGAAAAA 50304349

SEQ ID NO: 42:
Chr7: 50304322 CCCTATACCG AAACAACGAT

CCAAAAAA 50304349

SEQ ID NO: 43:
Chr7: 50304322 CCCTATACCA AAACAACAAT

CCGAAAAA 50304349

SEQ ID NO: 44:
Chr7: 50304322 CCCTATACCA AAACAACGAT

CCAAAAAA 50304349

SEQ ID NO: 45:
Chr7: 50304322 CCCTATACCG AAACAACAAT

CCAAAAAA 50304349

SEQ ID NO: 46:
Chr7: 50304322 CCCTATACCA AAACAACAAT

CCAAAAAA 50304349

SEQ ID NO: 47:
Chr7: 50304366 CGCGTATTTT TCGGTC 50304351

SEQ ID NO: 48:
Chr7: 50304273 CGACGCACCC TCTCCG 50304288
```

Examples of "Degenerate" Primers Designed to Amplify Partially Methylated IKZF1

```
                                  SEQ ID NO: 49
Chr7: 50304271 GATGACGTAT TTTTTTCGTG
TTTC 50304294 (IKZE1 FWD)

SEQ ID NO: 50
Chr7: 50304271 GACGATGTAT TTTTTTCGTG
TTTC 50304294 (IKZE1 FWD)

SEQ ID NO: 51
Chr7: 50304271 GACGACGTAT TTTTTTGTG
TTTC 50304294 (IKZE1 FWD)

SEQ ID NO: 52
Chr7: 50304271 GACGACGTAT TTTTTTCGTG
TTTT 50304294 (IKZE1 FWD)

SEQ ID NO: 53
Chr7: 50304271 GATGATGTAT TTTTTTCGTG
TTTC 50304294 (IKZE1 FWD)

SEQ ID NO: 54
Chr7: 50304271 GACGATGTAT TTTTTTTGTG
TTTC 50304294 (IKZE1 FWD)

SEQ ID NO: 55
Chr7: 50304271 GACGACGTAT TTTTTTTGTG
TTTT 50304294 (IKZE1 FWD)

SEQ ID NO: 56
Chr7: 50304271 GATGACGTAT TTTTTTTGTG
TTTC 50304294 (IKZE1 FWD)

SEQ ID NO: 57
Chr7: 50304271 GACGATGTAT TTTTTTCGTG
TTTT 50304294 (IKZE1 FWD)

SEQ ID NO: 58
Chr7: 50304271 GATGACGTAT TTTTTTCGTG
TTTT 50304294 (IKZE1 FWD)

SEQ ID NO: 59
Chr7: 50304271 GATGATGTAT TTTTTTTGTG
TTTC 50304294 (IKZE1 FWD)

SEQ ID NO: 60
Chr7: 50304271 GATGATGTAT TTTTTTCGTG
TTTT 50304294 (IKZE1 FWD)

SEQ ID NO: 61
Chr7: 50304271 GATGACGTAT TTTTTTTGTG
TTTT 50304294 (IKZE1 FWD)

SEQ ID NO: 62
Chr7: 50304271 GACGATGTAT TTTTTTTGTG
TTTT 50304294 (IKZE1 FWD)

SEQ ID NO: 63
Chr7: 50304365 ACGCACCTCT CGACCG
50304350 (IKZF1 REV)
```

-continued

```
                                  SEQ ID NO: 64
Chr7: 50304365 GCACACCTCT CGACCG
50304350 (IKZF1 REV)

SEQ ID NO: 65
Chr7: 50304365 GCGCACCTCT CAACCG
50304350 (IKZF1 REV)

SEQ ID NO: 66
Chr7: 50304365 GCGCACCTCT nCGACCA
50304350 (IKZF1 REV)

SEQ ID NO: 67
Chr7: 50304365 ACACACCTCT CGACCG
50304350 (IKZF1 REV)

SEQ ID NO: 68
Chr7: 50304365 GCACACCTCT CAACCG
50304350 (IKZF1 REV)

SEQ ID NO: 69
Chr7: 50304365 GCGCACCTCT CAACCA
50304350 (IKZF1 REV)

SEQ ID NO: 70
Chr7: 50304365 ACGCACCTCT CAACCG
50304350 (IKZF1 REV)

SEQ ID NO: 71
Chr7: 50304365 ACGCACCTCT CGACCA
50304350 (IKZF1 REV)

SEQ ID NO: 72
Chr7: 50304365 GCACACCTCT CGACCA
50304350 (IKZF1 REV)

SEQ ID NO: 73
Chr7: 50304365 ACACACCTCT CAACCG
50304350 (IKZF1 REV)

SEQ ID NO: 74
Chr7: 50304365 ACACACCTCT CGACCA
50304350 (IKZF1 REV)

SEQ ID NO: 75
Chr7: 50304365 ACGCACCTCT CAACCA
50304350 (IKZF1 REV)

SEQ ID NO: 76
Chr7: 50304365 GCACACCTCT CAACCA
50304350 (IKZF1 REV)

Fully unmethylated primers:
                                  SEQ ID NO: 77
Chr7: 50304271 GATGATGTAT TTTTTTGTG
TTT 50304294 (IKZF1 FWD)

SEQ ID NO: 78
Chr7: 50304365 ACACACCTCT CAACCA
50304350 (IKZF1 REV)
```

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Beaucage, et al. *Tetrahedron Letters* 22: 1859-1862, 1981;
Breslauer et al., *Proc. Natl. Acad. Sci. USA,* 83: 3746-3750, 1986;
Caruthers, M. H., et al., "Methods in Enzymology," Vol. 154, pp. 287-314 (1988);
Cottrell et al., *Nucl. Acids Res.* 32: e10, 2004;
Eads et al., *Nucl. Acids Res.* 28: E32, 2000;
Egholm et al., *Am. Chem. Soc.,* 114: 1895, 1992;
Egholm et al., *Nature,* 365: 566, 1993;
Gait (Ed) (In: Oligonucleotide Synthesis: A Practical Approach, IRL Press, Oxford, 1984);
Gibson et al., *Genome Res.* 6:995-1001, 1996;
Heid et al., *Genome Res.* 6:986-994, 1996;
Hill et al., *Proc Natl Acad Sci USA.,* 95:4258-4263, 1998;
Holland et al., *Proc. Natl. Acad. Sci. USA,* 88, 7276-7280, 1991;
Lee et al., *Nucleic Acid Res.* 21, 3761-3766, 1993;
Liu and Jia, 2014; *J Genet Genomics.* 41(1):21-33
Livak et al., *PCR Methods Appl.* 4:357-362, 1995;
Messing, *Methods Enzymol,* 101, 20-78, 1983;
Mhlanga and Malmberg, *Methods* 25:463-471, 2001;
Narang, et al. *Meth. Enzymol* 68: 90, 1979;
"Synthesis and Applications of DNA and RNA," S. A. Narang, editor, Academic Press, New York, 1987
Nielsen et al., *J. Chem. Soc. Perkin Trans.,* 1:3423, 1997
Orum et al., *Nucl. Acids Res.,* 21: 5332, 1993
Orum et al., *Clin. Chem.* 45: 1898-1905, 1999;
Simeonov and Nikiforov, *Nucleic Acids Research,* 30(17): 1-5, 2002;
Santa Lucia, *Proc. Natl. Acad. Sci. USA,* 95: 1460-1465, 1995
Singh and Wengel, *Chem. Commun.* 1247, 1998

The invention claimed is:

1. A method for detecting the cytosine methylation of a nucleic acid target of interest, said method comprising:
   (i) contacting a nucleic acid sample with an agent which modifies unmethylated cytosine residues;
   (ii) measuring within a single reaction, regions of partial methylation in a DNA form of the nucleic acid sample of step (i) by contacting the DNA with:
      (a) a primer set comprising forward and reverse primers designed to amplify one or more partially methylated forms of a region of cytosine methylation; and
      (b) one or more probes directed to said region of cytosine methylation wherein said one or more probes are capable of collectively hybridising to at least two differing methylation patterns at said region and wherein said probe comprises a detectable moiety;
   (iii) amplifying the sample of step (ii), wherein the extension of said primers along said target of interest effects the detection of said hybridised probe; and,
   (iv) qualitatively or quantitatively analysing the detection output of step (iii).

2. The method according to claim 1, wherein said nucleic acid target of interest is a DNA or RNA gene or gene region.

3. The method according to claim 2, wherein said gene region is a promoter region.

4. The method according to claim 2, wherein said gene is a mammalian gene.

5. The method according to claim 2, wherein said gene is a large intestine neoplasm marker.

6. The method according to claim 5, wherein said large intestine neoplasm marker is the gene BCAT1, IKZF1, IRF4, GRASP, CAHM, SOX21, SLC6A15, NPY, ST8SIA1, ZSCAN18, COL4A2, DLX5, FGF5, FOXF1, FOXI2 or SDC2, wherein said gene includes 5 kb upstream of the transcription start site.

7. The method according to claim 6, wherein said gene is IKZF1.

8. The method according to claim 7, wherein said method comprises detecting methylation at one or more of the Chr7:50304323-50304349, Chr7:50303300-50304923 or Chr7:50399869-50400702 regions of the IKZF1 gene.

9. The method according to claim 1, wherein said DNA is genomic DNA.

10. The method according to claim 1, wherein said agent modifies unmethylated cytosine residues to uracil.

11. The method according to claim 10, wherein said agent is a bisulphite salt.

12. The method according to claim 11, wherein said bisulphite salt is sodium bisulphite or ammonium bisulphite.

13. The method according to claim 1, wherein said primers are methylation specific primers.

14. The method according to claim 1, wherein said probes are hydrolysis probes.

15. The method according to claim 1, wherein said probes collectively hybridise to all full and partial methylation patterns at said region.

16. The method according to claim 1, wherein said nucleic acid target is IKZF1 and the primer set includes primers which comprise one or more of:
   (i) the SEQ ID NO:3 and SEQ ID NO:4 sequences or a sequence exhibiting at least 95% identity;
   (ii) the SEQ ID NO:49-62 and SEQ ID NO:63-76 sequences or a sequence exhibiting at least 95% identity; or
   (iii) the SEQ ID NO:77 and SEQ ID NO:78 sequences or a sequence exhibiting at least 95% identity.

17. The method according to claim 1, wherein said nucleic acid target is IKZF1 and the probe set includes probes which comprise one or more of:
   (i) the SEQ ID NO:5-12 sequences or a sequence exhibiting at least 95% identity;
   (ii) the SEQ ID NO:19 sequence or a sequence exhibiting at least 95% identity;
   (iii) the SEQ ID NO:20 sequence or a sequence exhibiting at least 95% identity; or (iv) the SEQ ID NO:23-30 sequences or a sequence exhibiting at least 95% identity.

18. The method according to claim 1, wherein said nucleic acid target is IKZF1, said DNA of step (ii) is a bisulfite converted DNA strand that is the complement of SEQ ID NO:1 and the primer set includes primers which comprise one or both of the SEQ ID NO:47 and SEQ ID NO:48 sequences or a sequence exhibiting at least 95% identity.

19. The method according to claim 1 wherein said nucleic acid target is IKZF1, said DNA of step (ii) is a bisulfite converted DNA strand that is the complement of SEQ ID NO:1 and the probe set includes probes which comprise one or more of:
(i) the SEQ ID NO:21 sequence or a sequence exhibiting at least 95% identity;
(ii) the SEQ ID NO:22 sequence or a sequence exhibiting at least 95% identity;
(iii) the SEQ ID NO:31-38 sequences or a sequence exhibiting at least 95% identity; and/or the SEQ ID NO:39-46 sequences or a sequence exhibiting at least 95% identity.

20. A diagnostic kit for detecting the cytosine methylation of a region of a nucleic acid target of interest, said kit comprising:
(i) a primer set comprising forward and reverse primers designed to amplify one or more partially methylated forms of a DNA form of said nucleic acid region in which unmethylated cytosine residues have been modified, wherein the primer set includes primers which comprise a sequence as set forth in:
(a) SEQ ID NO: 3 and SEQ ID NO: 4 or a sequence exhibiting at least 95% identity;
(b) SEQ ID NO: 47 and SEQ ID NO: 48 or a sequence exhibiting at least 95% identity;
(c) SEQ ID NOs: 49-62 and SEQ ID NOs: 63-76 or a sequence exhibiting at least 95% identity; or
(d) SEQ ID NO: 77 and SEQ ID NO: 78 or a sequence exhibiting at least 95% identity; and
(ii) one or more probes directed to the regions of partial cytosine methylation of the DNA of step (i) which probes are capable of collectively hybridising to at least two differing methylation patterns, wherein the one or more probes include probes comprising a sequence as set forth in:
(a) SEQ ID Nos: 5-12 or a sequence exhibiting at least 95% identity;
(b) SEQ ID NO: 19 or a sequence exhibiting at least 95% identity;
(c) SEQ ID NO: 20 or a sequence exhibiting at least 95% identity;
(d) SEQ ID NO: 21 or a sequence exhibiting at least 95% identity;
(e) SEQ ID NO: 22 or a sequence exhibiting at least 95% identity;
(f) SEQ ID NOs: 23-30 or a sequence exhibiting at least 95% identity;
(g) SEQ ID NOs: 31-38 or a sequence exhibiting at least 95% identity; or
(h) SEQ ID NOs: 39-46 or a sequence exhibiting at least 95% identity.

21. The kit according to claim 20, wherein said primers are methylation specific primers.

22. The kit according to claim 20, wherein said probes are hydrolysis probes.

23. The kit according to claim 20, wherein said probes collectively hybridise to all of the full and partial methylation patterns of said region.

24. The kit according to claim 20, wherein said kit additionally comprises an agent which modifies unmethylated cytosine residues.

25. The kit according to claim 24, wherein said agent is a bisulphite salt.

26. The kit according to claim 25, wherein said bisulphite salt is sodium bisulphite or ammonium bisulphite.

27. The kit according to claim 20, wherein said kit additionally comprises reagents to effect DNA amplification and/or detection.

28. The kit according to claim 20, wherein said nucleic acid target of interest is IKZF1.

29. The kit according to claim 28, wherein said primers and probes are directed to detecting methylation at one or more of the Chr7:50304323-50304349, Chr7:50303300-50304923 or Chr7:50399869-50400702 regions of the IKZF1 gene.

30. The kit according to claim 1, wherein said nucleic acid target is IKZF1, and the primer set includes primers which comprise one or both of the SEQ ID NO:47 and SEQ ID NO:48 sequences or sequence exhibiting at least 95% identity.

31. The kit according to claim 28, wherein said nucleic acid target is IKZF1, and the one or more probes comprise one or more of:
(i) the SEQ ID NO:21 sequence or a sequence exhibiting at least 95% identity;
(ii) the SEQ ID NO:22 sequence or a sequence exhibiting at least 95% identity; or
(iii) the SEQ ID NO:31-38 sequences or a sequence exhibiting at least 95% identity; and/or the SEQ ID NO:39-46 sequences or a sequence exhibiting at least 95% identity.

* * * * *

```
SEQUENCE LISTING

<160> NUMBER OF SEQ ID NOS: 86

<210> SEQ ID NO 1
<211> LENGTH: 95
<212> TYPE: DNA
<213> ORGANISM: Homo sapiens

<400> SEQUENCE: 1
gacgacgcac cctctccgtg tcccgctctg cgccttctg cgcgccccgc tccctgtacc      60
ggagcagcga tccgggaggc ggccgagagg tgcgc                                95

<210> SEQ ID NO 2
<211> LENGTH: 96
<212> TYPE: DNA
<213> ORGANISM: Artificial Sequence
<220> FEATURE:
<223> OTHER INFORMATION: bisulfite converted and fully methylated
      version of diagnostic IKZF1 amplicon

<400> SEQUENCE: 2
gacgacgtat tttttcgtg tttcgttttg cgttttttg cgcgtttcgc ttttgtatc        60 ggagtagcga ttcgggaggc ggtcgagagg tgcgcg                               96

<210> SEQ ID NO 3
<211> LENGTH: 24
<212> TYPE: DNA
<213> ORGANISM: Artificial Sequence
<220> FEATURE:
<223> OTHER INFORMATION: primer directed to partially methylated
      diagnostic IKZF1 amplicon

<400> SEQUENCE: 3
gacgacgtat tttttcgtg tttc                                             24

<210> SEQ ID NO 4
<211> LENGTH: 16
<212> TYPE: DNA
<213> ORGANISM: Artificial Sequence
<220> FEATURE:
<223> OTHER INFORMATION: primer directed to partially methylated
      diagnostic IKZF1 amplicon

<400> SEQUENCE: 4
```

```
gcgcacctct cgaccg                                                        16

<210> SEQ ID NO 5
<211> LENGTH: 27
<212> TYPE: DNA
<213> ORGANISM: Artificial Sequence
<220> FEATURE:
<223> OTHER INFORMATION: probe directed to partially methylated
      diagnostic IKZF1 amplicon

<400> SEQUENCE: 5
tttgtatcgg agtagcgatt cgggagg                                            27

<210> SEQ ID NO 6
<211> LENGTH: 27
<212> TYPE: DNA
<213> ORGANISM: Artificial Sequence
<220> FEATURE:
<223> OTHER INFORMATION: probe directed to partially methylated
      diagnostic IKZF1 amplicon

<400> SEQUENCE: 6
tttgtatcgg agtagcgatt tgggagg                                            27

<210> SEQ ID NO 7
<211> LENGTH: 27
<212> TYPE: DNA
<213> ORGANISM: Artificial Sequence
<220> FEATURE:
<223> OTHER INFORMATION: probe directed to partially methylated
      diagnostic IKZF1 amplicon

<400> SEQUENCE: 7
tttgtatcgg agtagtgatt cgggagg                                            27

<210> SEQ ID NO 8
<211> LENGTH: 27
<212> TYPE: DNA
<213> ORGANISM: Artificial Sequence
<220> FEATURE:
<223> OTHER INFORMATION: probe directed to partially methylated
      diagnostic IKZF1 amplicon

<400> SEQUENCE: 8
tttgtattgg agtagcgatt cgggagg                                            27

<210> SEQ ID NO 9
<211> LENGTH: 27
<212> TYPE: DNA
<213> ORGANISM: Artificial Sequence
<220> FEATURE:
<223> OTHER INFORMATION: probe directed to partially methylated
      diagnostic IKZF1 amplicon

<400> SEQUENCE: 9
tttgtatcgg agtagtgatt tgggagg                                            27

<210> SEQ ID NO 10
<211> LENGTH: 27
<212> TYPE: DNA
<213> ORGANISM: Artificial Sequence
<220> FEATURE:
<223> OTHER INFORMATION: probe directed to partially methylated
      diagnostic IKZF1 amplicon

<400> SEQUENCE: 10
tttgtattgg agtagcgatt tgggagg                                            27
```

<210> SEQ ID NO 11
<211> LENGTH: 27
<212> TYPE: DNA
<213> ORGANISM: Artificial Sequence
<220> FEATURE:
<223> OTHER INFORMATION: probe directed to partially methylated
      diagnostic IKZF1 amplicon

<400> SEQUENCE: 11
tttgtattgg agtagtgatt cgggagg                                      27

<210> SEQ ID NO 12
<211> LENGTH: 27
<212> TYPE: DNA
<213> ORGANISM: Artificial Sequence
<220> FEATURE:
<223> OTHER INFORMATION: probe directed to partially methylated
      diagnostic IKZF1 amplicon

<400> SEQUENCE: 12
tttgtattgg agtagtgatt tgggagg                                      27

<210> SEQ ID NO 13
<211> LENGTH: 29
<212> TYPE: DNA
<213> ORGANISM: Artificial Sequence
<220> FEATURE:
<223> OTHER INFORMATION: primer directed to BCAT1

<400> SEQUENCE: 13 gttttttttgt tgatgtaatt cgttaggtc                                   29

<210> SEQ ID NO 14
<211> LENGTH: 20
<212> TYPE: DNA
<213> ORGANISM: Artificial Sequence
<220> FEATURE:
<223> OTHER INFORMATION: primer directed to BCAT1

<400> SEQUENCE: 14
caatacccga aacgacgacg                                              20

<210> SEQ ID NO 15
<211> LENGTH: 21
<212> TYPE: DNA
<213> ORGANISM: Artificial Sequence
<220> FEATURE:
<223> OTHER INFORMATION: probe directed to BCAT1

<400> SEQUENCE: 15
ttcgtcgcga gagggtcggt t                                            21

<210> SEQ ID NO 16
<211> LENGTH: 25
<212> TYPE: DNA
<213> ORGANISM: Artificial Sequence
<220> FEATURE:
<223> OTHER INFORMATION: primer directed to ACTB1

<400> SEQUENCE: 16 ggagttttttg tttttttggtt agttg                                      25

<210> SEQ ID NO 17
<211> LENGTH: 29
<212> TYPE: DNA

```
<213> ORGANISM: Artificial Sequence
<220> FEATURE:
<223> OTHER INFORMATION: primer directed to ACTB1

<400> SEQUENCE: 17
caaaataaaa tacaaaacaa acctaatcc                                    29

<210> SEQ ID NO 18
<211> LENGTH: 34
<212> TYPE: DNA
<213> ORGANISM: Artificial Sequence
<220> FEATURE:
<223> OTHER INFORMATION: probe directed to ACTB1

<400> SEQUENCE: 18
atggaggttt agtggtaata taggttttgt ttgg                              34

<210> SEQ ID NO 19
<211> LENGTH: 27
<212> TYPE: DNA
<213> ORGANISM: Artificial Sequence
<220> FEATURE:
<223> OTHER INFORMATION: probe directed to partially methylated
      diagnostic IKZF1 amplicon
<220> FEATURE:
<221> NAME/KEY: misc_feature
<222> LOCATION: (8)..(8)
<223> OTHER INFORMATION: n is either inosine; an abasic spacer; or
      6H,8H-3,4-dihydropyrimido[4,5-c][1,2]oxazin-7-one (or a
      functional analogue thereof)
<220> FEATURE:
<221> NAME/KEY: misc_feature
<222> LOCATION: (16)..(16)
<223> OTHER INFORMATION: n is either inosine; an abasic spacer; or
      6H,8H-3,4-dihydropyrimido[4,5-c][1,2]oxazin-7-one (or a
      functional analogue thereof)
<220> FEATURE:
<221> NAME/KEY: misc_feature
<222> LOCATION: (21)..(21)
<223> OTHER INFORMATION: n is either inosine; an abasic spacer; or
      6H,8H-3,4-dihydropyrimido[4,5-c][1,2]oxazin-7-one (or a
      functional analogue thereof)

<400> SEQUENCE: 19
tttgtatngg agtagngatt ngggagg                                      27

<210> SEQ ID NO 20
<211> LENGTH: 29
<212> TYPE: DNA
<213> ORGANISM: Artificial Sequence
<220> FEATURE:
<223> OTHER INFORMATION: probe directed to partially methylated
      diagnostic IKZF1 amplicon
<220> FEATURE:
<221> NAME/KEY: misc_feature
<222> LOCATION: (6)..(6)
<223> OTHER INFORMATION: n is either inosine; an abasic spacer; or
      N6-methoxy-2,6-diaminopurine (or a functional analogue thereof)
<220> FEATURE:
<221> NAME/KEY: misc_feature
<222> LOCATION: (11)..(11)
<223> OTHER INFORMATION: n is either inosine; an abasic spacer; or
      N6-methoxy-2,6-diaminopurine (or a functional analogue thereof)
<220> FEATURE:
<221> NAME/KEY: misc_feature
<222> LOCATION: (19)..(19)
<223> OTHER INFORMATION: n is either inosine; an abasic spacer; or
      N6-methoxy-2,6-diaminopurine (or a functional analogue thereof)

<400> SEQUENCE: 20
ctcccnaatc nctactccna tacaaaaag                                    29
```

```
<210> SEQ ID NO 21
<211> LENGTH: 28
<212> TYPE: DNA
<213> ORGANISM: Artificial Sequence
<220> FEATURE:
<223> OTHER INFORMATION: probe directed to partially methylated
      diagnostic IKZF1 amplicon
<220> FEATURE:
<221> NAME/KEY: misc_feature
<222> LOCATION: (6)..(6)
<223> OTHER INFORMATION: n is either inosine; an abasic spacer; or
      6H,8H-3,4-dihydropyrimido[4,5-c][1,2]oxazin-7-one (or a
      functional analogue thereof)
<220> FEATURE:
<221> NAME/KEY: misc_feature
<222> LOCATION: (11)..(11)
<223> OTHER INFORMATION: n is either inosine; an abasic spacer; or
      6H,8H-3,4-dihydropyrimido[4,5-c][1,2]oxazin-7-one (or a
      functional analogue thereof)
<220> FEATURE:
<221> NAME/KEY: misc_feature
<222> LOCATION: (19)..(19)
<223> OTHER INFORMATION: n is either inosine; an abasic spacer; or
      6H,8H-3,4-dihydropyrimido[4,5-c][1,2]oxazin-7-one (or a
      functional analogue thereof)

<400> SEQUENCE: 21
tttttnggat ngttgtttng gtatagggg                                       28

<210> SEQ ID NO 22
<211> LENGTH: 28
<212> TYPE: DNA
<213> ORGANISM: Artificial Sequence
<220> FEATURE:
<223> OTHER INFORMATION: probe directed to partially methylated
      diagnostic IKZF1 amplicon
<220> FEATURE:
<221> NAME/KEY: misc_feature
<222> LOCATION: (10)..(10)
<223> OTHER INFORMATION: n is either inosine; an abasic spacer; or
      N6-methoxy-2,6-diaminopurine (or a functional analogue thereof)
<220> FEATURE:
<221> NAME/KEY: misc_feature
<222> LOCATION: (18)..(18)
<223> OTHER INFORMATION: n is either inosine; an abasic spacer; or
      N6-methoxy-2,6-diaminopurine (or a functional analogue thereof)
<220> FEATURE:
<221> NAME/KEY: misc_feature
<222> LOCATION: (23)..(23)
<223> OTHER INFORMATION: n is either inosine; an abasic spacer; or
      N6-methoxy-2,6-diaminopurine (or a functional analogue thereof)

<400> SEQUENCE: 22
ccctataccn aaacaacnat ccnaaaaa                                        28

<210> SEQ ID NO 23
<211> LENGTH: 29
<212> TYPE: DNA
<213> ORGANISM: Artificial Sequence
<220> FEATURE:
<223> OTHER INFORMATION: probe for detection of the sense strand of SEQ
      ID NO:2

<400> SEQUENCE: 23
ctcccgaatc gctactccga tacaaaaag                                       29

<210> SEQ ID NO 24
<211> LENGTH: 29
<212> TYPE: DNA
<213> ORGANISM: Artificial Sequence
<220> FEATURE:
<223> OTHER INFORMATION: probe for detection of the sense strand of SEQ
```

ID NO:2

<400> SEQUENCE: 24
ctcccaaatc gctactccga tacaaaaag                                29

<210> SEQ ID NO 25
<211> LENGTH: 29
<212> TYPE: DNA
<213> ORGANISM: Artificial Sequence
<220> FEATURE:
<223> OTHER INFORMATION: probe for detection of the sense strand of SEQ
      ID NO:2

<400> SEQUENCE: 25
ctcccgaatc actactccga tacaaaaag                                29

<210> SEQ ID NO 26
<211> LENGTH: 29
<212> TYPE: DNA
<213> ORGANISM: Artificial Sequence
<220> FEATURE:
<223> OTHER INFORMATION: probe for detection of the sense strand of SEQ
      ID NO:2

<400> SEQUENCE: 26
ctcccgaatc gctactccaa tacaaaaag                                29

<210> SEQ ID NO 27
<211> LENGTH: 29
<212> TYPE: DNA
<213> ORGANISM: Artificial Sequence
<220> FEATURE:
<223> OTHER INFORMATION: probe for detection of the sense strand of SEQ
      ID NO:2

<400> SEQUENCE: 27
ctcccaaatc actactccga tacaaaaag                                29

<210> SEQ ID NO 28
<211> LENGTH: 29
<212> TYPE: DNA
<213> ORGANISM: Artificial Sequence
<220> FEATURE:
<223> OTHER INFORMATION: probe for detection of the sense strand of SEQ
      ID NO:2

<400> SEQUENCE: 28
ctcccaaatc gctactccaa tacaaaaag                                29

<210> SEQ ID NO 29
<211> LENGTH: 29
<212> TYPE: DNA
<213> ORGANISM: Artificial Sequence
<220> FEATURE:
<223> OTHER INFORMATION: probe for detection of the sense strand of SEQ
      ID NO:2

<400> SEQUENCE: 29
ctcccgaatc actactccaa tacaaaaag                                29

<210> SEQ ID NO 30
<211> LENGTH: 29
<212> TYPE: DNA
<213> ORGANISM: Artificial Sequence
<220> FEATURE:
<223> OTHER INFORMATION: probe for detection of the sense strand of SEQ
      ID NO:2

<210> SEQ ID NO 31
<211> LENGTH: 28
<212> TYPE: DNA
<213> ORGANISM: Artificial Sequence
<220> FEATURE:
<223> OTHER INFORMATION: probe for detection of the bisulfite converted
      version of the complementary strand of SEQ ID NO:1

<400> SEQUENCE: 30
ctcccaaatc actactccaa tacaaaaag                                        29

<210> SEQ ID NO 31
<211> LENGTH: 28
<212> TYPE: DNA
<213> ORGANISM: Artificial Sequence
<220> FEATURE:
<223> OTHER INFORMATION: probe for detection of the bisulfite converted
      version of the complementary strand of SEQ ID NO:1

<400> SEQUENCE: 31
tttttcggat cgttgtttcg gtataggg                                         28

<210> SEQ ID NO 32
<211> LENGTH: 28
<212> TYPE: DNA
<213> ORGANISM: Artificial Sequence
<220> FEATURE:
<223> OTHER INFORMATION: probe for detection of the bisulfite converted
      version of the complementary strand of SEQ ID NO:1

<400> SEQUENCE: 32
tttttcggat cgttgttttg gtataggg                                         28

<210> SEQ ID NO 33
<211> LENGTH: 28
<212> TYPE: DNA
<213> ORGANISM: Artificial Sequence
<220> FEATURE:
<223> OTHER INFORMATION: probe for detection of the bisulfite converted
      version of the complementary strand of SEQ ID NO:1

<400> SEQUENCE: 33
tttttcggat tgttgtttcg gtataggg                                         28

<210> SEQ ID NO 34
<211> LENGTH: 28
<212> TYPE: DNA
<213> ORGANISM: Artificial Sequence
<220> FEATURE:
<223> OTHER INFORMATION: probe for detection of the bisulfite converted
      version of the complementary strand of SEQ ID NO:1

<400> SEQUENCE: 34 tttttggat cgttgtttcg gtataggg                                          28

<210> SEQ ID NO 35
<211> LENGTH: 28
<212> TYPE: DNA
<213> ORGANISM: Artificial Sequence
<220> FEATURE:
<223> OTHER INFORMATION: probe for detection of the bisulfite converted
      version of the complementary strand of SEQ ID NO:1

<400> SEQUENCE: 35
tttttcggat tgttgttttg gtataggg                                         28

<210> SEQ ID NO 36
<211> LENGTH: 28
<212> TYPE: DNA
<213> ORGANISM: Artificial Sequence
<220> FEATURE:
<223> OTHER INFORMATION: probe for detection of the bisulfite converted
      version of the complementary strand of SEQ ID NO:1

```
<400> SEQUENCE: 36 tttttggat cgttgttttg gtataggg                                      28

<210> SEQ ID NO 37
<211> LENGTH: 28
<212> TYPE: DNA
<213> ORGANISM: Artificial Sequence
<220> FEATURE:
<223> OTHER INFORMATION: probe for detection of the bisulfite converted
      version of the complementary strand of SEQ ID NO:1

<400> SEQUENCE: 37 tttttggat tgttgtttcg gtataggg                                      28

<210> SEQ ID NO 38
<211> LENGTH: 28
<212> TYPE: DNA
<213> ORGANISM: Artificial Sequence
<220> FEATURE:
<223> OTHER INFORMATION: probe for detection of the bisulfite converted
      version of the complementary strand of SEQ ID NO:1

<400> SEQUENCE: 38 tttttggat tgttgttttg gtataggg                                      28

<210> SEQ ID NO 39
<211> LENGTH: 28
<212> TYPE: DNA
<213> ORGANISM: Artificial Sequence
<220> FEATURE:
<223> OTHER INFORMATION: probe for detection of the bisulfite converted
      version of the complementary strand of SEQ ID NO:1

<400> SEQUENCE: 39
ccctataccg aaacaacgat ccgaaaaa                                     28

<210> SEQ ID NO 40
<211> LENGTH: 28
<212> TYPE: DNA
<213> ORGANISM: Artificial Sequence
<220> FEATURE:
<223> OTHER INFORMATION: probe for detection of the bisulfite converted
      version of the complementary strand of SEQ ID NO:1

<400> SEQUENCE: 40
ccctatacca aaacaacgat ccgaaaaa                                     28

<210> SEQ ID NO 41
<211> LENGTH: 28
<212> TYPE: DNA
<213> ORGANISM: Artificial Sequence
<220> FEATURE:
<223> OTHER INFORMATION: probe for detection of the bisulfite converted
      version of the complementary strand of SEQ ID NO:1

<400> SEQUENCE: 41
ccctataccg aaacaacaat ccgaaaaa                                     28

<210> SEQ ID NO 42
<211> LENGTH: 28
<212> TYPE: DNA
<213> ORGANISM: Artificial Sequence
<220> FEATURE:
<223> OTHER INFORMATION: probe for detection of the bisulfite converted
      version of the complementary strand of SEQ ID NO:1

<400> SEQUENCE: 42
```

```
ccctataccg aaacaacgat ccaaaaaa                                              28
```

<210> SEQ ID NO 43
<211> LENGTH: 28
<212> TYPE: DNA
<213> ORGANISM: Artificial Sequence
<220> FEATURE:
<223> OTHER INFORMATION: probe for detection of the bisulfite converted
      version of the complementary strand of SEQ ID NO:1

<400> SEQUENCE: 43

```
ccctatacca aaacaacaat ccgaaaaa                                              28
```

<210> SEQ ID NO 44
<211> LENGTH: 28
<212> TYPE: DNA
<213> ORGANISM: Artificial Sequence
<220> FEATURE:
<223> OTHER INFORMATION: probe for detection of the bisulfite converted
      version of the complementary strand of SEQ ID NO:1

<400> SEQUENCE: 44

```
ccctatacca aaacaacgat ccaaaaaa                                              28
```

<210> SEQ ID NO 45
<211> LENGTH: 28
<212> TYPE: DNA
<213> ORGANISM: Artificial Sequence
<220> FEATURE:
<223> OTHER INFORMATION: probe for detection of the bisulfite converted
      version of the complementary strand of SEQ ID NO:1

<400> SEQUENCE: 45

```
ccctataccg aaacaacaat ccaaaaaa                                              28
```

<210> SEQ ID NO 46
<211> LENGTH: 28
<212> TYPE: DNA
<213> ORGANISM: Artificial Sequence
<220> FEATURE:
<223> OTHER INFORMATION: probe for detection of the bisulfite converted
      version of the complementary strand of SEQ ID NO:1

<400> SEQUENCE: 46

```
ccctatacca aaacaacaat ccaaaaaa                                              28
```

<210> SEQ ID NO 47
<211> LENGTH: 16
<212> TYPE: DNA
<213> ORGANISM: Artificial Sequence
<220> FEATURE:
<223> OTHER INFORMATION: probe for detection of the bisulfite converted
      version of the complementary strand of SEQ ID NO:1

<400> SEQUENCE: 47

```
cgcgtatttt tcggtc                                                          16
```

<210> SEQ ID NO 48
<211> LENGTH: 16
<212> TYPE: DNA
<213> ORGANISM: Artificial Sequence
<220> FEATURE:
<223> OTHER INFORMATION: probe for detection of the bisulfite converted
      version of the complementary strand of SEQ ID NO:1

<400> SEQUENCE: 48
cgacgcaccc tctccg                                                    16

<210> SEQ ID NO 49
<211> LENGTH: 24
<212> TYPE: DNA
<213> ORGANISM: Artificial Sequence
<220> FEATURE:
<223> OTHER INFORMATION: primer directed to partially methylated IKZF1

<400> SEQUENCE: 49
gatgacgtat tttttcgtg tttc                                            24

<210> SEQ ID NO 50
<211> LENGTH: 24
<212> TYPE: DNA
<213> ORGANISM: Artificial Sequence
<220> FEATURE:
<223> OTHER INFORMATION: primer directed to partially methylated IKZF1

<400> SEQUENCE: 50
gacgatgtat tttttcgtg tttc                                            24

<210> SEQ ID NO 51
<211> LENGTH: 24
<212> TYPE: DNA
<213> ORGANISM: Artificial Sequence
<220> FEATURE:
<223> OTHER INFORMATION: primer directed to partially methylated IKZF1

<400> SEQUENCE: 51
gacgacgtat tttttttgtg tttc                                           24

<210> SEQ ID NO 52
<211> LENGTH: 24
<212> TYPE: DNA
<213> ORGANISM: Artificial Sequence
<220> FEATURE:
<223> OTHER INFORMATION: primer directed to partially methylated IKZF1

<400> SEQUENCE: 52
gacgacgtat tttttcgtg tttt                                            24

<210> SEQ ID NO 53
<211> LENGTH: 24
<212> TYPE: DNA
<213> ORGANISM: Artificial Sequence
<220> FEATURE:
<223> OTHER INFORMATION: primer directed to partially methylated IKZF1

<400> SEQUENCE: 53
gatgatgtat tttttcgtg tttc                                            24

<210> SEQ ID NO 54
<211> LENGTH: 24
<212> TYPE: DNA
<213> ORGANISM: Artificial Sequence
<220> FEATURE:
<223> OTHER INFORMATION: primer directed to partially methylated IKZF1

<400> SEQUENCE: 54
gacgatgtat tttttttgtg tttc                                           24

<210> SEQ ID NO 55
<211> LENGTH: 24
<212> TYPE: DNA
<213> ORGANISM: Artificial Sequence

```
<220> FEATURE:
<223> OTHER INFORMATION: primer directed to partially methylated IKZF1

<400> SEQUENCE: 55
gacgacgtat tttttttgtg tttt                                              24

<210> SEQ ID NO 56
<211> LENGTH: 24
<212> TYPE: DNA
<213> ORGANISM: Artificial Sequence
<220> FEATURE:
<223> OTHER INFORMATION: primer directed to partially methylated IKZF1

<400> SEQUENCE: 56
gatgacgtat tttttttgtg tttc                                              24

<210> SEQ ID NO 57
<211> LENGTH: 24
<212> TYPE: DNA
<213> ORGANISM: Artificial Sequence
<220> FEATURE:
<223> OTHER INFORMATION: primer directed to partially methylated IKZF1

<400> SEQUENCE: 57
gacgatgtat tttttcgtg tttt                                               24

<210> SEQ ID NO 58
<211> LENGTH: 24
<212> TYPE: DNA
<213> ORGANISM: Artificial Sequence
<220> FEATURE:
<223> OTHER INFORMATION: primer directed to partially methylated IKZF1

<400> SEQUENCE: 58
gatgacgtat tttttcgtg tttt                                               24

<210> SEQ ID NO 59
<211> LENGTH: 24
<212> TYPE: DNA
<213> ORGANISM: Artificial Sequence
<220> FEATURE:
<223> OTHER INFORMATION: primer directed to partially methylated IKZF1

<400> SEQUENCE: 59
gatgatgtat tttttttgtg tttc                                              24

<210> SEQ ID NO 60
<211> LENGTH: 24
<212> TYPE: DNA
<213> ORGANISM: Artificial Sequence
<220> FEATURE:
<223> OTHER INFORMATION: primer directed to partially methylated IKZF1

<400> SEQUENCE: 60
gatgatgtat tttttcgtg tttt                                               24

<210> SEQ ID NO 61
<211> LENGTH: 24
<212> TYPE: DNA
<213> ORGANISM: Artificial Sequence
<220> FEATURE:
<223> OTHER INFORMATION: primer directed to partially methylated IKZF1

<400> SEQUENCE: 61
gatgacgtat tttttttgtg tttt                                              24
```

<210> SEQ ID NO 62
<211> LENGTH: 24
<212> TYPE: DNA
<213> ORGANISM: Artificial Sequence
<220> FEATURE:
<223> OTHER INFORMATION: primer directed to partially methylated IKZF1

<400> SEQUENCE: 62
gacgatgtat tttttttgtg tttt                                        24

<210> SEQ ID NO 63
<211> LENGTH: 16
<212> TYPE: DNA
<213> ORGANISM: Artificial Sequence
<220> FEATURE:
<223> OTHER INFORMATION: primer directed to partially methylated IKZF1

<400> SEQUENCE: 63
acgcacctct cgaccg                                                 16

<210> SEQ ID NO 64
<211> LENGTH: 16
<212> TYPE: DNA
<213> ORGANISM: Artificial Sequence
<220> FEATURE:
<223> OTHER INFORMATION: primer directed to partially methylated IKZF1

<400> SEQUENCE: 64
gcacacctct cgaccg                                                 16

<210> SEQ ID NO 65
<211> LENGTH: 16
<212> TYPE: DNA
<213> ORGANISM: Artificial Sequence
<220> FEATURE:
<223> OTHER INFORMATION: primer directed to partially methylated IKZF1

<400> SEQUENCE: 65
gcgcacctct caaccg                                                 16

<210> SEQ ID NO 66
<211> LENGTH: 16
<212> TYPE: DNA
<213> ORGANISM: Artificial Sequence
<220> FEATURE:
<223> OTHER INFORMATION: primer directed to partially methylated IKZF1

<400> SEQUENCE: 66
gcgcacctct cgacca                                                 16

<210> SEQ ID NO 67
<211> LENGTH: 16
<212> TYPE: DNA
<213> ORGANISM: Artificial Sequence
<220> FEATURE:
<223> OTHER INFORMATION: primer directed to partially methylated IKZF1

<400> SEQUENCE: 67
acacacctct cgaccg                                                 16

<210> SEQ ID NO 68
<211> LENGTH: 16
<212> TYPE: DNA
<213> ORGANISM: Artificial Sequence
<220> FEATURE:
<223> OTHER INFORMATION: primer directed to partially methylated IKZF1

<400> SEQUENCE: 68
gcacacctct caaccg                    16

<210> SEQ ID NO 69
<211> LENGTH: 16
<212> TYPE: DNA
<213> ORGANISM: Artificial Sequence
<220> FEATURE:
<223> OTHER INFORMATION: primer directed to partially methylated IKZF1

<400> SEQUENCE: 69
gcacacctct caaccg                    16

<210> SEQ ID NO 70
<211> LENGTH: 16
<212> TYPE: DNA
<213> ORGANISM: Artificial Sequence
<220> FEATURE:
<223> OTHER INFORMATION: primer directed to partially methylated IKZF1

<400> SEQUENCE: 70
acgcacctct caaccg                    16

<210> SEQ ID NO 71
<211> LENGTH: 16
<212> TYPE: DNA
<213> ORGANISM: Artificial Sequence
<220> FEATURE:
<223> OTHER INFORMATION: primer directed to partially methylated IKZF1

<400> SEQUENCE: 71
acgcacctct cgacca                    16

<210> SEQ ID NO 72
<211> LENGTH: 16
<212> TYPE: DNA
<213> ORGANISM: Artificial Sequence
<220> FEATURE:
<223> OTHER INFORMATION: primer directed to partially methylated IKZF1

<400> SEQUENCE: 72
gcacacctct cgacca                    16

<210> SEQ ID NO 73
<211> LENGTH: 16
<212> TYPE: DNA
<213> ORGANISM: Artificial Sequence
<220> FEATURE:
<223> OTHER INFORMATION: primer directed to partially methylated IKZF1

<400> SEQUENCE: 73
acacacctct caaccg                    16

<210> SEQ ID NO 74
<211> LENGTH: 16
<212> TYPE: DNA
<213> ORGANISM: Artificial Sequence
<220> FEATURE:
<223> OTHER INFORMATION: primer directed to partially methylated IKZF1

<400> SEQUENCE: 74
acacacctct cgacca                    16

<210> SEQ ID NO 75

-continued

```
<211> LENGTH: 16
<212> TYPE: DNA
<213> ORGANISM: Artificial Sequence
<220> FEATURE:
<223> OTHER INFORMATION: primer directed to partially methylated IKZF1

<400> SEQUENCE: 75
acgcacctct caacca                                                        16

<210> SEQ ID NO 76
<211> LENGTH: 16
<212> TYPE: DNA
<213> ORGANISM: Artificial Sequence
<220> FEATURE:
<223> OTHER INFORMATION: primer directed to partially methylated IKZF1

<400> SEQUENCE: 76
gcacacctct caacca                                                        16

<210> SEQ ID NO 77
<211> LENGTH: 24
<212> TYPE: DNA
<213> ORGANISM: Artificial Sequence
<220> FEATURE:
<223> OTHER INFORMATION: fully unmethylated primer

<400> SEQUENCE: 77
gatgatgtat tttttttgtg tttt                                               24

<210> SEQ ID NO 78
<211> LENGTH: 16
<212> TYPE: DNA
<213> ORGANISM: Artificial Sequence
<220> FEATURE:
<223> OTHER INFORMATION: fully unmethylated primer

<400> SEQUENCE: 78
acacacctct caacca                                                        16

<210> SEQ ID NO 79
<211> LENGTH: 27
<212> TYPE: DNA
<213> ORGANISM: Artificial Sequence
<220> FEATURE:
<223> OTHER INFORMATION: IKZF1
<220> FEATURE:
<221> NAME/KEY: misc_feature
<222> LOCATION: (8)..(8)
<223> OTHER INFORMATION: n represents a methylated cytosine
<220> FEATURE:
<221> NAME/KEY: misc_feature
<222> LOCATION: (16)..(16)
<223> OTHER INFORMATION: n represents a methylated cytosine
<220> FEATURE:
<221> NAME/KEY: misc_feature
<222> LOCATION: (21)..(21)
<223> OTHER INFORMATION: n represents a methylated cytosine

<400> SEQUENCE: 79
cctgtacngg agcagngatc ngggagg                                            27

<210> SEQ ID NO 80
<211> LENGTH: 27
<212> TYPE: DNA
<213> ORGANISM: Artificial Sequence
<220> FEATURE:
<223> OTHER INFORMATION: IKZF1
<220> FEATURE:
<221> NAME/KEY: misc_feature
```

```
<222> LOCATION: (16)..(16)
<223> OTHER INFORMATION: n represents a methylated cytosine
<220> FEATURE:
<221> NAME/KEY: misc_feature
<222> LOCATION: (21)..(21)
<223> OTHER INFORMATION: n represents a methylated cytosine

<400> SEQUENCE: 80
cctgtaccgg agcagngatc ngggagg                                              27

<210> SEQ ID NO 81
<211> LENGTH: 27
<212> TYPE: DNA
<213> ORGANISM: Artificial Sequence
<220> FEATURE:
<223> OTHER INFORMATION: IKZF1
<220> FEATURE:
<221> NAME/KEY: misc_feature
<222> LOCATION: (8)..(8)
<223> OTHER INFORMATION: n represents a methylated cytosine
<220> FEATURE:
<221> NAME/KEY: misc_feature
<222> LOCATION: (21)..(21)
<223> OTHER INFORMATION: n represents a methylated cytosine

<400> SEQUENCE: 81
cctgtacngg agcagcgatc ngggagg                                              27

<210> SEQ ID NO 82
<211> LENGTH: 27
<212> TYPE: DNA
<213> ORGANISM: Artificial Sequence
<220> FEATURE:
<223> OTHER INFORMATION: IKZF1
<220> FEATURE:
<221> NAME/KEY: misc_feature
<222> LOCATION: (8)..(8)
<223> OTHER INFORMATION: n represents a methylated cytosine
<220> FEATURE:
<221> NAME/KEY: misc_feature
<222> LOCATION: (16)..(16)
<223> OTHER INFORMATION: n represents a methylated cytosine

<400> SEQUENCE: 82
cctgtacngg agcagngatc cgggagg                                              27

<210> SEQ ID NO 83
<211> LENGTH: 27
<212> TYPE: DNA
<213> ORGANISM: Artificial Sequence
<220> FEATURE:
<223> OTHER INFORMATION: IKZF1
<220> FEATURE:
<221> NAME/KEY: misc_feature
<222> LOCATION: (21)..(21)
<223> OTHER INFORMATION: n represents a methylated cytosine

<400> SEQUENCE: 83
cctgtaccgg agcagcgatc ngggagg                                              27

<210> SEQ ID NO 84
<211> LENGTH: 27
<212> TYPE: DNA
<213> ORGANISM: Artificial Sequence
<220> FEATURE:
<223> OTHER INFORMATION: IKZF1
<220> FEATURE:
<221> NAME/KEY: misc_feature
<222> LOCATION: (16)..(16)
<223> OTHER INFORMATION: n represents a methylated cytosine
```

```
<400> SEQUENCE: 84
cctgtaccgg agcagngatc cgggagg                                              27

<210> SEQ ID NO 85
<211> LENGTH: 27
<212> TYPE: DNA
<213> ORGANISM: Artificial Sequence
<220> FEATURE:
<223> OTHER INFORMATION: IKZF1
<220> FEATURE:
<221> NAME/KEY: misc_feature
<222> LOCATION: (8)..(8)
<223> OTHER INFORMATION: n represents a methylated cytosine

<400> SEQUENCE: 85
cctgtacngg agcagcgatc cgggagg                                              27

<210> SEQ ID NO 86
<211> LENGTH: 27
<212> TYPE: DNA
<213> ORGANISM: Artificial Sequence
<220> FEATURE:
<223> OTHER INFORMATION: IKZF1

<400> SEQUENCE: 86
cctgtaccgg agcagcgatc cgggagg                                              27
```